(12) United States Patent
Altschuler

(10) Patent No.: US 12,350,159 B2
(45) Date of Patent: Jul. 8, 2025

(54) OPTIMIZED CAGE SYSTEMS PROMOTING BONE REPAIR AND FUSION

(71) Applicant: CARTIHEAL (2009) LTD., Kfar Saba (IL)

(72) Inventor: Nir Altschuler, Tsur Yitskhak (IL)

(73) Assignee: CARTIHEAL (2009) LTD., Kfar Saba (IL)

( * ) Notice: Subject to any disclaimer, the term of this patent is extended or adjusted under 35 U.S.C. 154(b) by 557 days.

(21) Appl. No.: 17/275,739

(22) PCT Filed: Sep. 15, 2019

(86) PCT No.: PCT/IL2019/051030
§ 371 (c)(1),
(2) Date: Mar. 12, 2021

(87) PCT Pub. No.: WO2020/053867
PCT Pub. Date: Mar. 19, 2020

(65) Prior Publication Data
US 2022/0054271 A1    Feb. 24, 2022

(30) Foreign Application Priority Data
Sep. 16, 2018   (IL) .......................................... 261820

(51) Int. Cl.
*A61F 2/44*       (2006.01)
*A61B 17/68*    (2006.01)
(Continued)

(52) U.S. Cl.
CPC ................ *A61F 2/30* (2013.01); *A61B 17/68* (2013.01); *A61F 2/08* (2013.01);
(Continued)

(58) Field of Classification Search
CPC .......... A61F 2310/00341; A61F 2/4455; A61F 2002/30622; A61F 2002/2835; A61F 2/447
See application file for complete search history.

(56) References Cited

U.S. PATENT DOCUMENTS 5,609,635 A * 3/1997 Michelson ............ A61F 2/4455
   606/907
7,435,261 B1 * 10/2008 Castro ....................... A61F 2/44
   623/17.11
(Continued)

OTHER PUBLICATIONS

International Search Report (ISR) for PCT/IL2019/051030 (Int'l Filing Date: Sep. 15, 2019), mailed Jan. 1, 2020, from the European Patent Office, Rijswijk, Netherlands, 5 pages.
(Continued)

*Primary Examiner* — Javier G Blanco
(74) *Attorney, Agent, or Firm* — Seager, Tufte & Wickhem LLP

(57) ABSTRACT

This invention provides, inter alia, a device having a cage having an opening or window in at least one of its walls that allows for the insertion of bone growth promoting materials therethrough, comprising one or more openings in one or more of the walls of the cage, designed to receive bone growth promoting materials, including coral-based materials, which facilitate in the fusion with the treated bone, and which optionally serves to reinforce the stability of the implanted structure. Methods of stabilizing two skeletal structures relative to one another, joining two skeletal structures which are discontinuous and repairing a ligament tear or replacing a ligament making use of a bone fusion device of the invention are described.

11 Claims, 7 Drawing Sheets

(51) Int. Cl.
   *A61F 2/08* (2006.01)
   *A61F 2/30* (2006.01)
   *A61F 2/46* (2006.01)

(52) U.S. Cl.
   CPC ............ *A61B 2017/681* (2013.01); *A61F 2002/30622* (2013.01); *A61F 2002/30754* (2013.01); *A61F 2002/3093* (2013.01); *A61F 2/4455* (2013.01); *A61F 2002/4632* (2013.01); *A61F 2310/00341* (2013.01)

(56) References Cited

U.S. PATENT DOCUMENTS

| | | |
|---|---|---|
| 8,790,681 B2 | 7/2014 | Altschuler et al. |
| 8,802,115 B2 | 8/2014 | Altschuler et al. |
| 8,808,725 B2 | 8/2014 | Altschuler et al. |
| 9,770,531 B2 | 9/2017 | Altschuler |
| 10,046,084 B2 | 8/2018 | Altschuler et al. |
| 10,080,818 B2 | 9/2018 | Altschuler et al. |
| 10,271,938 B2 | 4/2019 | Altschuler |
| 10,342,897 B2 | 7/2019 | Altschuler |
| 10,702,627 B2 | 7/2020 | Altschuler et al. |
| 10,799,251 B2 | 10/2020 | Altschuler et al. |
| 10,806,823 B2 | 10/2020 | Altschuler |
| 11,007,304 B2 | 5/2021 | Altschuler et al. |
| 11,116,873 B2 | 9/2021 | Altschuler |
| 2001/0016777 A1* | 8/2001 | Biscup .............. A61F 2/4455 623/17.16 |
| 2002/0128652 A1* | 9/2002 | Ferree .............. A61F 2/2846 606/279 |
| 2004/0053196 A1* | 3/2004 | Mayer .............. A61B 17/70 433/173 |
| 2008/0154314 A1* | 6/2008 | McDevitt ........... A61F 2/447 623/13.14 |
| 2008/0281431 A1 | 11/2008 | Missos |
| 2014/0303733 A1 | 10/2014 | Davis |
| 2015/0134065 A1* | 5/2015 | Altschuler ......... A61L 27/3604 623/23.72 |
| 2016/0166301 A1* | 6/2016 | Papangelou ....... A61B 17/7035 606/232 |
| 2016/0361467 A1 | 12/2016 | Klimek et al. |
| 2017/0333205 A1* | 11/2017 | Joly ................ A61F 2/30771 |

OTHER PUBLICATIONS

International Preliminary Report on Patentability and Written Opinion for PCT/IL2019/051030 (Int'l Filing Date: Sep. 15, 2019), completed Mar. 16, 2021, by the European Patent Office, Berlin, Germany, 7 pages.

* cited by examiner

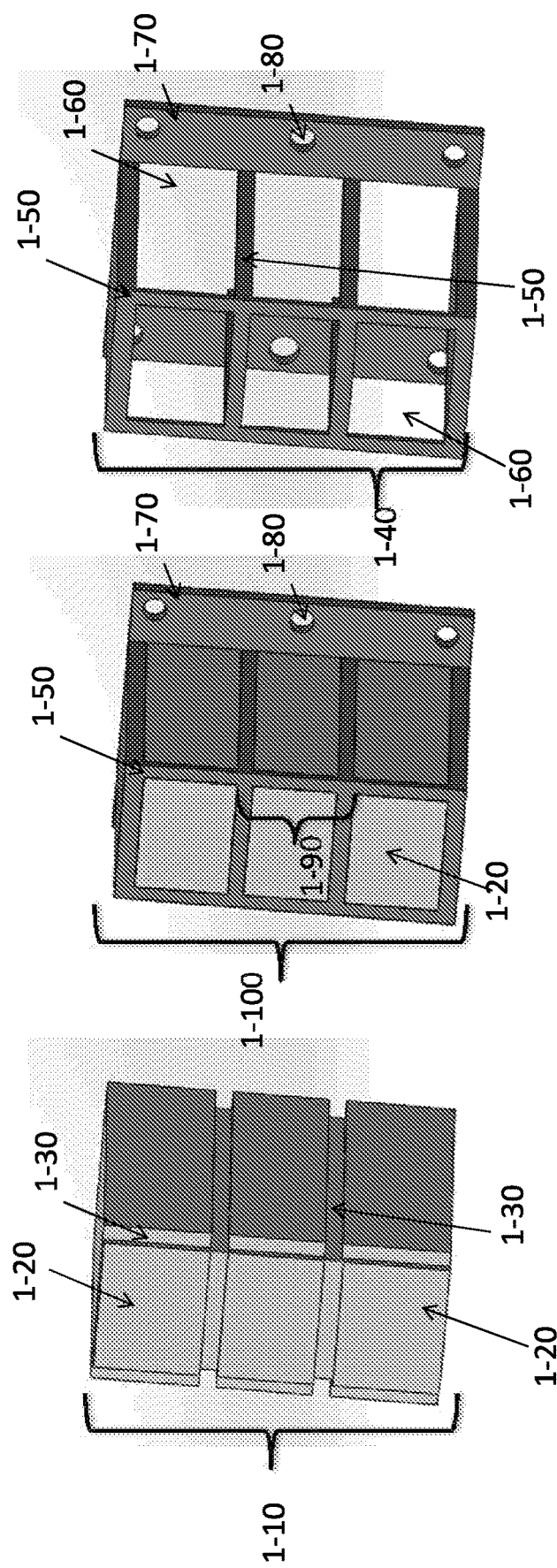

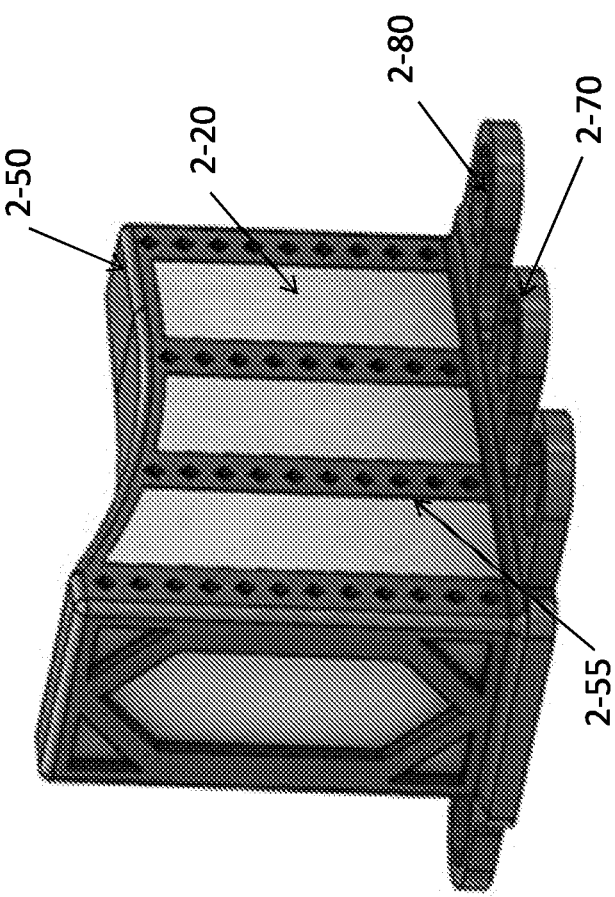
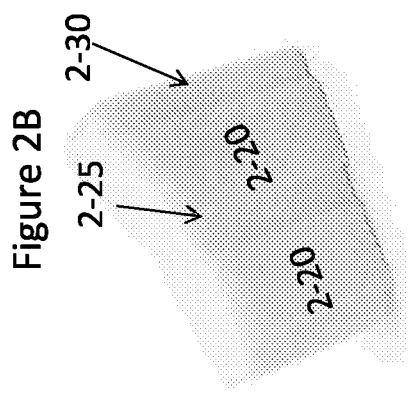
Figure 2B
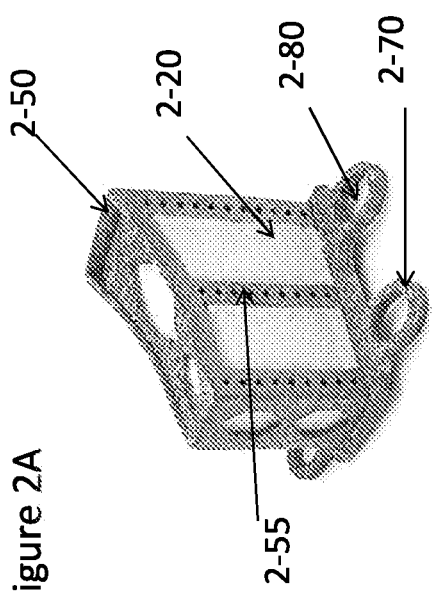
Figure 2D
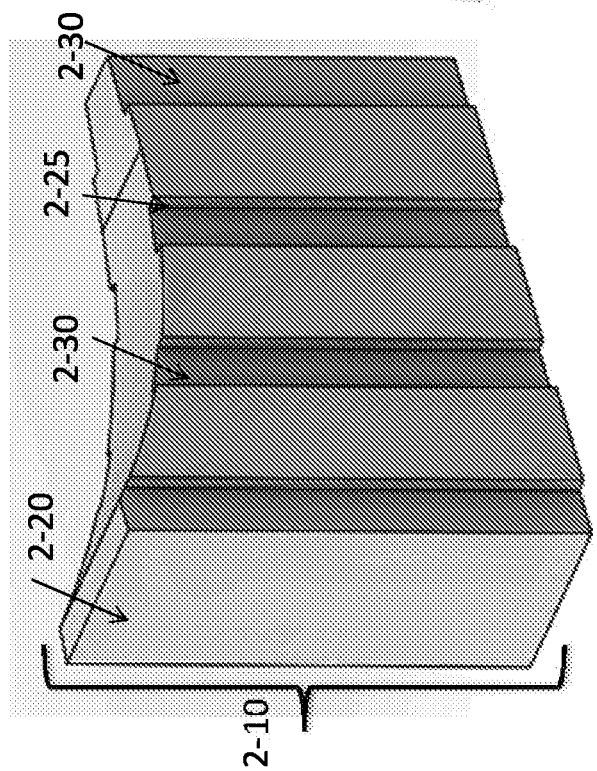
Figure 2A
Figure 2C

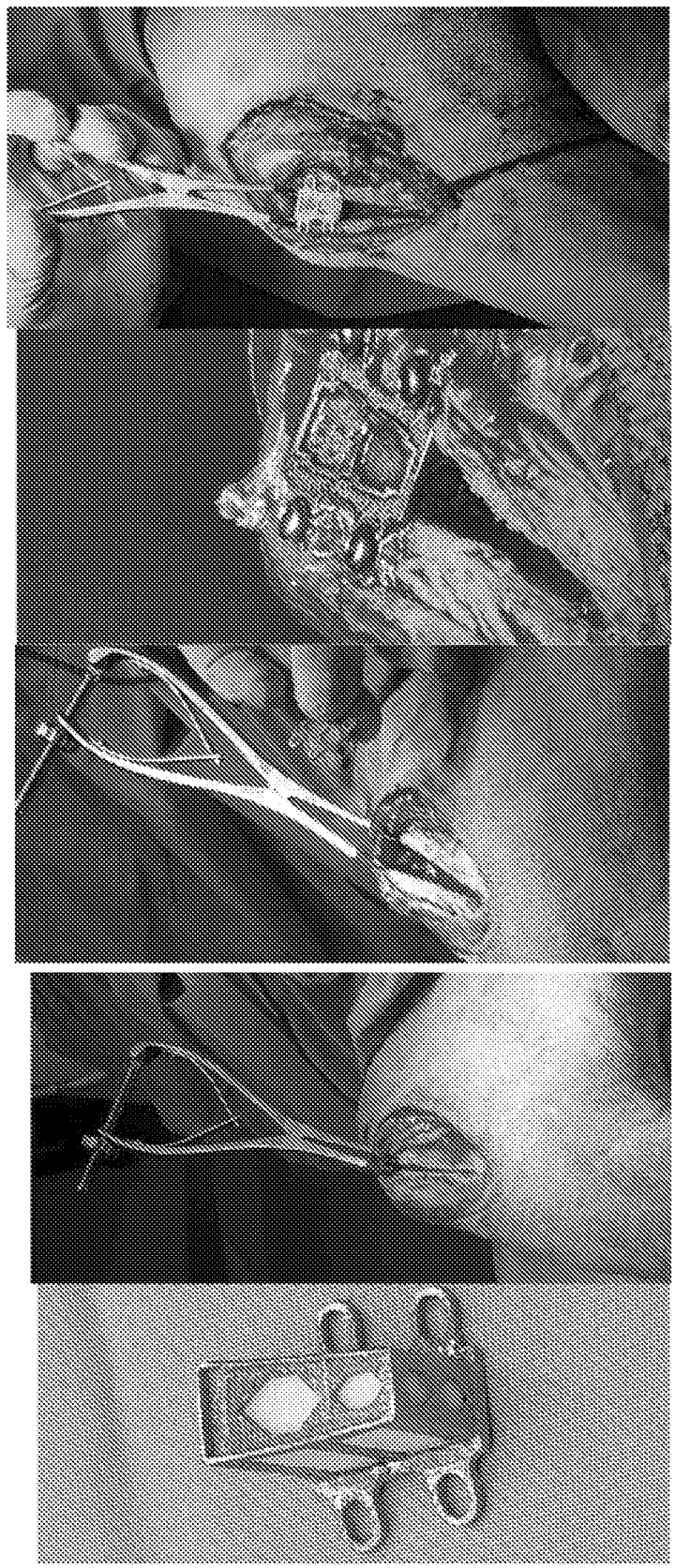

OPTIMIZED CAGE SYSTEMS PROMOTING BONE REPAIR AND FUSION

BACKGROUND OF THE INVENTION

Skeletal bone fixation systems are used during surgical reconstruction of skeletal segments to bridge bony gaps and to adjust, align and fixate the remaining bone or bony fragments. Surgical resection of bone often employs same and the subsequent reconstruction of the skeletal segment is a common procedure. Implantable devices bridging the region of bone resection and providing structural support for the remaining skeletal segment are typically used. These devices are especially useful in spinal surgery where they are used to restore spinal alignment and to stabilize the spinal column after vertebral and/or disc resection.

While these devices provide immediate structural support of the operative segment, long term stability requires that a replacement for the resected bone is included and that the grafted bone successfully incorporate ("fuse") within the skeletal segment. For these reasons, many devices are designed with a rigid outer structure that is intended to provide immediate stability and a hollow central cavity that is used to retain the bone graft while the bony fusion proceeds.

A number of difficulties still remain with the many prosthetic implants currently available. While it is recognized that hollow implants which permit bone in-growth in the bone or bone substitute within the implant is an optimum technique for achieving fusion, most of these devices have difficulty achieving this fusion, at least without the aid of some additional stabilizing device, such as a rod or plate. Moreover, some of these devices are not structurally strong enough to support heavy loads applied e.g. at the most frequently fused vertebral levels, such as in the lower lumbar spine.

There remains a need for providing a prosthetic implant that optimizes the bone ingrowth capabilities while being strong enough to support the healing bone until fusion occurs.

An ideal material which satisfied these criteria and facilitates reconstruction of the morphology of such tissue is as yet, lacking.

SUMMARY OF THE INVENTION

The present invention relates to a device having a bone fusion device comprising a cage frame having an opening or window in at least one of its frame elements that allows for the insertion of bone graft promoting material therethrough to be flush with the outer limits of the cage frame elements after the bone fusion device has been placed in situ, to facilitate in the positioning of the bone fusion device in the affected region for desired bone healing/treatment, and/or securing the cage in place and/or fixation of anything to bone and/or for promoting physical connection between two bones and/or stabilizing and/or treating ligament repair and/or graft replacement.

In some aspects the bone graft promoting material of which the insert is comprised includes, inter alia, bone-derived materials, including autologous bone or allograft, bamboo, or any natural bone mimetic material or any other appropriate solid bone growth-promoting material. In some aspects, the bone graft promoting material of which the insert is comprised of coral, including solid coral or ground coral particles provided in a solid matrix. In some embodiments, the bone graft promoting material comprises coralline-based materials, such as converted hydroxyapatite, enriched coral, including coral enriched for elemental components such as silicium, and others as will be appreciated by the skilled artisan.

In some aspects, the fusion device comprises one or more openings in one or more of the frame elements of the cage frame, designed to receive bone graft promoting materials, including coral-based materials, which facilitate in the fusion of the affected bone, and which optionally serves to reinforce the stability of the implanted structure.

In some embodiments, this invention provides a bone fusion device forming a rigid structure between adjoining regions in one or more bones comprising a cage frame defined by a top cage frame element, a bottom cage frame element and lateral cage frame elements, said top cage frame element and said bottom cage frame element designed to be positionable between and be at least partially load bearing for a surface of an adjacent bone, and wherein at least one of said top and bottom cage frame element include an opening to receive a bone growth promoting material, which facilitates the fusion of said one or more bones, and which optionally serves to reinforce the stability of the implanted fusion device between said adjoining regions in said one or more bones, wherein said bone growth promoting material is comprised of a solid block which block is machined or structurally modified to include a modified surface of said bone growth promoting material into which at least a portion of at least one cage frame element inserts seamlessly therein so that an outer face of said bone growth promoting material is neither protruding nor recessed with respect to said at least one cage frame element.

In some aspects, the device is suitable for intervertebral fusion and according to this aspect, the device comprises one or more openings in one or more of the frame elements of the cage frame, designed to receive bone graft promoting materials, including coral-based materials, which facilitate in the fusion of the vertebrae, and which optionally serves to reinforce the stability of the implanted structure.

According to this aspect, such cage frame has one or more vertical through holes that connects to such window, so that bone growth promoting material may be placed through the window to fill the cavity of the cage. The bone growth promoting material is a solid machined or otherwise structurally modified block that contains extending regions, which are flush with the boundaries of the cage structure, so that the outer surface of cage and bone growth promoting material is contiguous and provides maximal exposure of the treated bone to the protruding bone growth-promoting material.

Further according to this aspect and in some embodiments, the fusion devices of this invention may further comprise a faceplate that covers a region of a frame element of the cage, to provide a template for screw holes that allow the device to be securely fixed, e.g. to the vertebral body or other bone structure.

The bone fusion devices of this invention provide improved prosthetic implants used to facilitate in the fusion of two or more bones. In some embodiments, such devices are intervertebral fusion devices, which provide improved prosthetic implants used to facilitate in the fusion of two or more vertebrae.

In some aspects, the bone fusion devices of this invention provide prosthetic implants used to facilitate adherence of desired structures/materials to bone, e.g. to connect between two proximal bones, for example, promoting healing of non-union fractures, gaps or voids in a bone, or in other aspects, to promote bridging of bone in cases where bone tumors are present/were excised, or in cases of bone necrosis, or for example, in cases of sinus lift in dental applications, or for example, in cases where fixing malalignment of bones is desired, or for example, in the treatment of rib cage injury, or for example, in cases of skull injury, and others, as will be appreciated by the skilled artisan In some aspects, the bone fusion devices of this invention provide prosthetic implants whereby the cage element is load bearing, i.e. provides structural support for the mechanical loads applied to the treated tissue regions, while the bone growth promoting materials, including coral-based materials, stimulate, enhance or otherwise promote bone remodeling, i.e. osteoconduction, osteointegration and/or osteotransduction.

In some aspects, the bone fusion devices of this invention provide prosthetic implants whereby the cage fixation can either permit or restrict mobility at the site of fixation.

In some aspects, the bone fusion devices of this invention provide prosthetic implants whereby the size, shape, overall dimensions, etc. may be designed and scaled based on information gleaned from imaging studies, such as MRI, CT, ultrasound, X-ray, or any appropriate imaging technique, as will be known to the skilled artisan.

In some embodiments, the invention provides a personalized bone fusion device as herein described, wherein the geometry of the device is customized to be suitable to accommodate the bone fusion device within a desired site of bone repair or bone joining as arrived at based on medical imaging assessments of the site of bone repair or bone joining, or other methods being treated with same, as described herein. In some aspects, the medical imaging assessment comprises CT or MRI scanning.

In accordance with the principal feature of the present invention, there is provided a prosthetic implant that is formed of a biologically compatible material for use in humans. The prosthetic implant is shaped and sized for insertion, in some aspects, between two bones such as vertebrae. In one specific embodiment, the prosthetic implant is designed to be placed in the intervertebral disk space that was formerly occupied by an intervertebral disk. The intervertebral disk is partially or completely removed prior to insertion of the prosthetic implant between the vertebrae.

In one specific embodiment, the shape and size of the device is selected to have an anatomically correct shape. In another embodiment, the prosthetic implant is shaped to increase the area of contact with the treated bone/s, e.g. vertebrae and/or to closely emulate the region treated, e.g. the region formerly occupied by the intervertebral disk.

In still another embodiment, the device is designed to be readily inserted by established surgical procedures, with minimal chances of surgical difficulty.

In yet another embodiment, the geometry of the device ensures proper load bearing, desired load bearing and support through the fused bone, e.g. vertebrae, minimizing the likelihood of the prosthetic implant dislocating relative to its positioning during surgery, e.g. relative to its positioning in the vertebrae either during surgery or during the post-operative fusing process.

In accordance with another aspect of the present invention, there is provided a prosthetic implant which includes a cage frame having a top cage frame element, a bottom cage frame element and lateral cage frame elements 1. In one embodiment, the cage frame is made of a material that is inert or biologically compatible with the vertebrae. The material of the cage frame includes, but is not limited to, bone, stainless steel, titanium, chrome, cobalt, polycarbonate, polypropylene, polyethylene, polymethylmethacrylate, polysulfone types filled with glass and/or carbon fibers, and various types of carbon and fiber reinforced polymers and any combination thereof. The material of the cage frame may also include, but is not limited to, nitinol, PEEK, a ceramic material, hydroxyapatite coated hard materials or a combination thereof.

In accordance with another embodiment, the cage frame is designed to maintain a tension load of about ten to forty pounds and more preferably about fifteen to thirty-five pounds on the disk tissue when used in appropriate applications related to same. This tension load facilitates in maintaining the cage frame in position, for example, between vertebrae and accelerates bone ingrowth bridging structures, e.g. between vertebrae. In still another embodiment, the cage frame is made of a material which closely approximates the elasticity of the structure being treated thereby.

In accordance with still another aspect of the present invention, the lateral cage frame elements of the prosthetic implant extends substantially along the longitudinal axis of the cage and wherein the lateral cage frame elements are configured to enhance the stability of the cage, for example, within the intervertebral disk space.

In one embodiment, the lateral cage frame element is at least partially arcuate.

In another embodiment, the lateral cage frame elements have different face configurations.

In one specific embodiment, a first lateral cage frame element includes an arcuate surface and a second side has a substantially flat or planar surface.

In one specific embodiment, the first lateral cage frame element has a substantially uniform arcuate surface.

In another specific embodiment, the actuate surface has a radius of curvature of about 2 to 30 degrees.

In cage configurations having an arcuate first lateral cage frame element surface, in some aspects, the cage is positioned in the intervertebral disk space such that the substantially flat or planar surface of the second side is positioned closely adjacent to the spinal cord and the first side is positioned adjacent the peripheral edge of the intervertebral disk space.

In some embodiments, prosthetic implant cages having an arcuate or curvilinear lateral cage frame element have been found to more closely conform to the surfaces with the intervertebral disk space thereby resulting in a higher degree of success for fusing together two vertebrae. The different side configurations of the cage frame also function as a visual aid to ensure that the cage is properly oriented between two vertebrae.

In accordance with yet another aspect of the present invention, the cage of the prosthetic implant includes a top cage frame element and/or a bottom cage frame element having at least one rigid surface adapted to engage the underside surface of a vertebra within the intervertebral disk space.

In one embodiment, the top cage frame element includes a plurality of ridged surfaces. In another embodiment, the bottom cage frame element includes a plurality of ridged surfaces. The ridged surfaces on the top and/or bottom cage frame element can have a number of configurations. In one specific embodiment, the ridges have diamond shaped surfaces, thereby functioning similar to teeth-like structures. In another specific embodiment, the ridge is a uniform structure extending over the lateral and/or longitudinal surface of the top and/or bottom cage frame element. In another embodiment, the ridges are positioned on the top end and/or bottom cage frame element and are spaced from the outer peripheral edge of the bottom and/or top cage frame element. In still another embodiment, the top and bottom cage frame element have similar ridge configurations and a similar number of ridges; however, it can be appreciated that the top and bottom cage frame element can have different numbers and/or different configurations of ridges. In still yet another embodiment, the ridges in the top and/or bottom cage frame element of the cage anchor the cage in between the vertebrae and provide channels for bone ingrowth which facilitates in the fusion of the vertebrae.

In accordance with still yet another aspect of the present invention, the cage frame of the prosthetic implant includes one or more openings in one or more of the cage frame elements of the cage. In one embodiment, the openings are designed to receive coral-based materials which facilitate in the fusion of the vertebrae, facilitate in the positioning of the cage between the vertebrae, and/or secure the cage in place within the intervertebral disk space.

In one specific embodiment, one or more of the openings are designed to receive a coral-based solid material which facilitates in the formation of a graft between two vertebrae and serves to reinforce the stability of the structure.

According to this aspect and in some embodiments, the material which facilitates in the formation of a graft between two vertebrae is comprised of solid coral, provided as one or more solid coral pieces, or in some embodiments, ground coral pieces that easily pack the defined area provided in the graft for the material.

In another specific embodiment, the cage includes still further openings to allow blood vessels to invade and the proximal bone and bone forming, as facilitated by the devices of this invention.

In still other specific embodiments, one or more openings in the cage are filled with the bone growth promoting materials, including coral-based materials, which may also promote growth out of the openings of the cage radially, longitudinally and/or vertically from the cage and grow into the bone tissue of the adjoining adjacent tissue.

In some embodiments, the bone growth promoting materials are coral-based materials, which facilitate in the fusion of treated proximal tissue and bone, such as, for example, the vertebrae, facilitate in the positioning of the cage between treated tissues, and/or secure the cage in place within the region, for example, the intervertebral disk space.

In some aspects, when the bone growth promoting materials are coral-based materials, the bone growth promoting materials including may be characterized by a specific fluid uptake capacity value of at least 75% or characterized by having a contact angle value of less than 60 degrees, when in contact with a biocompatible fluid, including blood, plasma, serum, platelet rich plasma, artificial blood as herein described, water, a protein-containing or carbohydrate containing solution, etc.

In some embodiments, the coral is aragonite, calcite, mixtures thereof, or other polymorphs of the same. In some embodiments, the solid substrate is isolated from a *Porites* species, a *Goniopora*, a *Millepora* species or an *Acropora* species.

In some embodiments, the coral-based materials as herein described are characterized by a specific fluid uptake capacity value of at least 75%, which specific fluid uptake capacity value is determined by establishing a spontaneous fluid uptake value divided by a total fluid uptake value, or in some aspects, more specifically established by a method comprising the steps of:

establishing a specific fluid uptake capacity value of said solid substrate, which specific fluid uptake capacity value is determined by establishing a spontaneous fluid uptake value divided by a total fluid uptake value;

selecting a coral-based material/s characterized by a specific fluid uptake capacity value of at least 75% or is characterized by having a contact angle value of less than 60 degrees; and utilizing a coral-based material/s characterized by a specific fluid uptake capacity value of at least 75% or is characterized by having a contact angle value of less than 60 degrees.

In some embodiments, according to this aspect, the process further comprises the step of prior contacting the coral-based materials with a fluid for from 0.5-15 minutes to promote spontaneous fluid uptake of said fluid within said coral-based materials to arrive at said spontaneous fluid uptake value.

In some embodiments, according to this aspect, the process further comprises the step of prior contacting said materials, including coral-based material/s with a fluid and applying negative pressure to said materials, including coral-based materials to promote maximal uptake of said fluid within said coral-based materials to arrive at said total fluid uptake value.

In some embodiments, according to this aspect, the specific fluid uptake capacity value is a function of change in weight in said materials, including coral-based material/s.

In some embodiments, according to this aspect, the change in weight in said coral-based material/s may be due to absorbance of said fluid within said material, for example, within interstices in said coral-based material/s, or in some embodiments, due to absorbance of said fluid within pores in said coral-based material/s.

In some embodiments, according to this aspect, the specific fluid uptake capacity value is a function of change in fluid volume of applied fluid to said coralline-based materials.

In some embodiments, a fluid is a protein-containing, salt-containing or carbohydrate containing solution, or in some embodiments, the fluid is a biologic fluid, and in some embodiments, the biologic fluid is autologous or allogeneic with respect to a cell or tissue of a subject when said solid substrate is contacted with a cell or tissue of said subject. In some embodiments, the fluid is water.

In still other specific embodiments, the top and/or bottom cage frame elements comprise an opening which communicates with an internal cavity of the cage. In still yet another embodiment, the top and bottom cage frame elements include at least one opening that are substantially the same shape and size.

In accordance with other embodiments, the lateral cage frame elements include at least one opening adapted to receive an instrument for guiding and/or inserting the cage at the site of treatment, such as, for example, between the vertebrae of the spine by an anterior, posterior, lateral and/or latroscopic approach into affected tissue, for example, in the spinal column. The openings allow a surgeon to select which approach is best for inserting the prosthetic implant as appropriate.

In accordance with other aspects of the present invention, at least one or more edges of the cage are rounded off so as not to be sharp. The rounding off of the edges reduces and/or eliminates damaging proximal tissue, for example, pinching of the nerve leading from the spinal cord which can result in pain, damage or paralysis to the individual. The rounded edges may minimize tissue injury, such as, for example, avoiding or minimizing nerve pressure that can be exerted on the nerves intervertebrally exiting the spinal cord.

In one specific embodiment, the lateral edges of the cage are rounded off. In other embodiments, all the edges of the cage are rounded off.

In accordance with still another aspect of the present invention, the top wall and/or bottom cage frame elements are at least partially inclined along the longitudinal axis of the cage. In one embodiment, the top wall and/or bottom cage frame elements are uniformly inclined from the back end to the front end.

In one specific embodiment, the back end cage frame element is higher than the front end cage frame element. In another specific embodiment, the angle of inclination of the top and/or bottom cage frame elements is about 0.5 to 15 degrees and preferably about 1 to 10 degrees and more preferably about 3 to 8 degrees.

The inclination of the top and/or bottom cage frame elements of the cage facilitates in the ease of insertion into the vertebrae column and/or provides a better fit for the cage within the intervertebral disk space since the inclination better matches the anatomical shape of the space between the vertebrae of the spinal column. In accordance with another embodiment, the inclined top and/or bottom cage frame elements of the cage accommodate the positioning of the cage between two vertebrae of the spinal column and the ridges on the top and/or bottom cage frame elements of the cage are adapted to contact the surfaces of the vertebrae bone and secure the cage in position between the vertebrae until the fusion of the vertebrae is complete.

In accordance with yet another aspect of the present invention, the top wall and/or bottom cage frame elements are at least partially inclined between the first and second side wall of the cage. In one embodiment, the top and/or bottom cage frame elements are uniformly inclined from the first and second lateral cage frame elements.

In one specific embodiment, the second side cage frame element is higher than the first side cage frame element. In another specific embodiment, the angle of inclination of the top and/or bottom cage frame elements is about 0.5 to 15 degrees and preferably about 1 to 10 degrees and more preferably about 3 to 8 degrees.

In accordance with another aspect of the present invention, multiple devices as described herein may be implanted as needed for tissue repair. According to this aspect and in some embodiments, a pair of cages is used to support and/or fuse two vertebrae in the spinal column. In one embodiment, the cages are positioned in a side by side relation to form a rigid transverse strut between adjacent vertebrae.

It is an object of the present invention to provide an improved prosthetic implant for insertion between a large fracture in a single bone, or in some embodiments, for insertion between two bones such as vertebrae and others.

It is another object of the present invention is to provide a prosthetic implant which better emulates the void created in the fracture space or the space between the bones, e.g. long bones, vertebrae and others.

Yet another object of the present invention to provide a prosthetic implant which includes one or more ridges to help secure the prosthetic implant in position.

It is yet another object of the present invention to provide a prosthetic implant which is used in a side by side relation to form a rigid transverse strut between adjacent regions of bone or between bones, for example, between vertebrae.

It is still yet another object of the present invention to provide a prosthetic implant which provides improved spinal support fixation and methodology which provides stability between adjacent vertebrae and the shape will facilitate in securing the prosthetic implant between the vertebrae.

In the intervertebral fusion devices of this invention, such device will comprise one or more openings that can receive material, which facilitates in the formation of a graft between two vertebrae and serves to reinforce the stability of the structure.

Surprisingly, the fusion devices of this invention can be easily and efficiently positioned, for example, in non-union fractures and reduces the failure rate of similar prosthetic implants existing in the art.

It is another object of the present invention to provide intervertebral fusion devices which includes one or more sloped surfaces to facilitate in the insertion of the prosthetic implant between the adjacently positioned vertebrae and to better match the shape of the prosthetic implant to the space between the adjacently positioned vertebrae.

It is still another object of the present invention to provide intervertebral fusion devices which includes surfaces that reduce pinching with the spinal cord and other body parts closely adjacent to the prosthetic implant.

In another embodiment of the invention there is provided a method for joining two skeletal structures, the method comprising: providing a bone fusion device as herein descried to be disposed between the two skeletal structures to be joined and securing said bone fusion device therebetween to promote bone remodeling and joining of said two skeletal structures.

In some embodiments, there is provided a method for joining two skeletal structures which are discontinuous, the method comprising: providing a bone fusion device as herein described to be disposed between the two skeletal structures and securing said bone fusion device therebetween to promote bone remodeling and joining of said discontinuous two skeletal structures.

According to this aspect, and in some embodiments, the method is utilized to join two skeletal structures in a non-union fracture.

In some embodiments, the invention provides a method for repairing a ligament tear or replacing a ligament, the method comprising: providing a bone fusion device as described herein to be disposed between at least one skeletal structure and ligament or graft affixing the ligament or graft to bone, to promote ligament repair and/or graft incorporation and stabilization, thereby being a method for repairing a ligament tear or replacing a ligament.

In some embodiments, the invention provides a method for repairing a ligament tear or replacing a ligament, the method comprising: providing a bone fusion device as herein described, wherein the ligament tear or injury results in the ligament being connected to a bone fragment from a larger bone to which the ligament is meant to be affixed and the bone fusion device as herein described is then disposed to join the two skeletal structures, i.e. the bone fragment and the larger bone to which the ligament is meant to be affixed, thereby being a method for repairing a ligament tear or replacing a ligament.

According to this aspect, and in some embodiments, the method is utilized for fixation of soft tissue into bony structures such as, for example, in ligamentous repair, ligamentous anchoring, as in Anterior Cruciate Ligament (ACL) and Posterior Cruciate Ligament (PCL) repair, rotator cuff repair, and others as will be understood to the skilled artisan.

These and other objects of the invention will become apparent to those skilled in the art upon reading and understanding the following detailed description of preferred embodiments taken together with the drawings.

All publications, patents, and patent applications mentioned herein are hereby incorporated by reference in their entirety as if each individual publication or patent was specifically and individually indicated to be incorporated by reference. In case of a conflict between the specification and an incorporated reference, the specification shall control. Where number ranges are given in this document, endpoints are included within the range. Furthermore, it is to be understood that unless otherwise indicated or otherwise evident from the context and understanding of one of ordinary skill in the art, values that are expressed as ranges can assume any specific value or sub-range within the stated ranges, optionally including or excluding either or both endpoints, in different embodiments of the invention, to the tenth of the unit of the lower limit of the range, unless the context clearly dictates otherwise. Where a percentage is recited in reference to a value that intrinsically has units that are whole numbers, any resulting fraction may be rounded to the nearest whole number.

BRIEF DESCRIPTION OF THE DRAWINGS

FIG. 1A-1C schematically describe an embodied bone fusion device of the invention. The cage frame and a bone growth promoting material is depicted, including a showing of a cage frame 1-40, comprising a bracketing structure 1-50, windowed regions 1-60 filled by protruding machined surfaces 1-20 of the bone growth promoting material and affixing region 1-70, containing access regions 1-80 through which affixing structures may be inserted to anchor the device to the bone being thereby treated.

FIGS. 2A-2F depict another embodied bone fusion device of this invention, where the bone growth promoting material 2-10 is contoured on a surface and also machined to provide surface exposed regions 2-20, and recessed regions 2-30, flanked by recessing regions 2-25, into which bracketing structures of the cage frame 2-55 insert in a tight fit manner FIGS. 2B and 2C schematically depict two embodied fusion devices of the invention, and FIGS. 2A and 2D depict the bone growth promoting material as it may be placed therein. FIGS. 2E and 2F depict the embodied bone growth promoting material and frame of FIGS. 2A and 2B, respectively, as viewed from a different angle.

FIGS. 4A-4E depict the embodied bone fusion device depicted schematically in FIG. 2C, and implantation of same in 6 goats who underwent Tibial Tuberosity Advancement surgery (TTA). The cage frame was made of titanium and the bone growth promoting material 1-10 comprised solid coral processed and prepared as described herein.

FIG. 5E depicts the embodied bone fusion device used in this procedure, where the bone growth promoting material (5-20) extends to be flush with the terminus of the titanium cage (5-50) so that the exposed surface area of the bone growth promoting material is in maximal contact with the bone to which the device is applied.

DETAILED DESCRIPTION OF THE PRESENT INVENTION

Figure 2E:
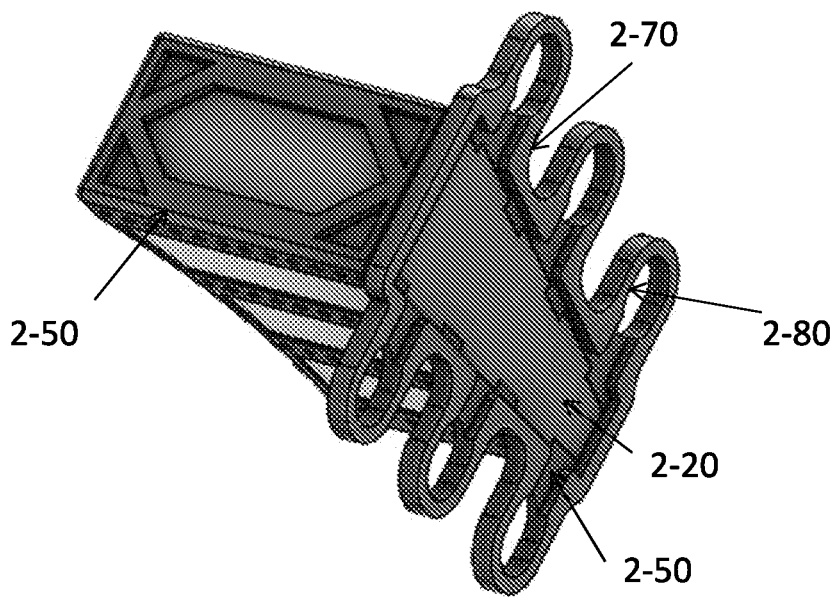
Figure 2F:
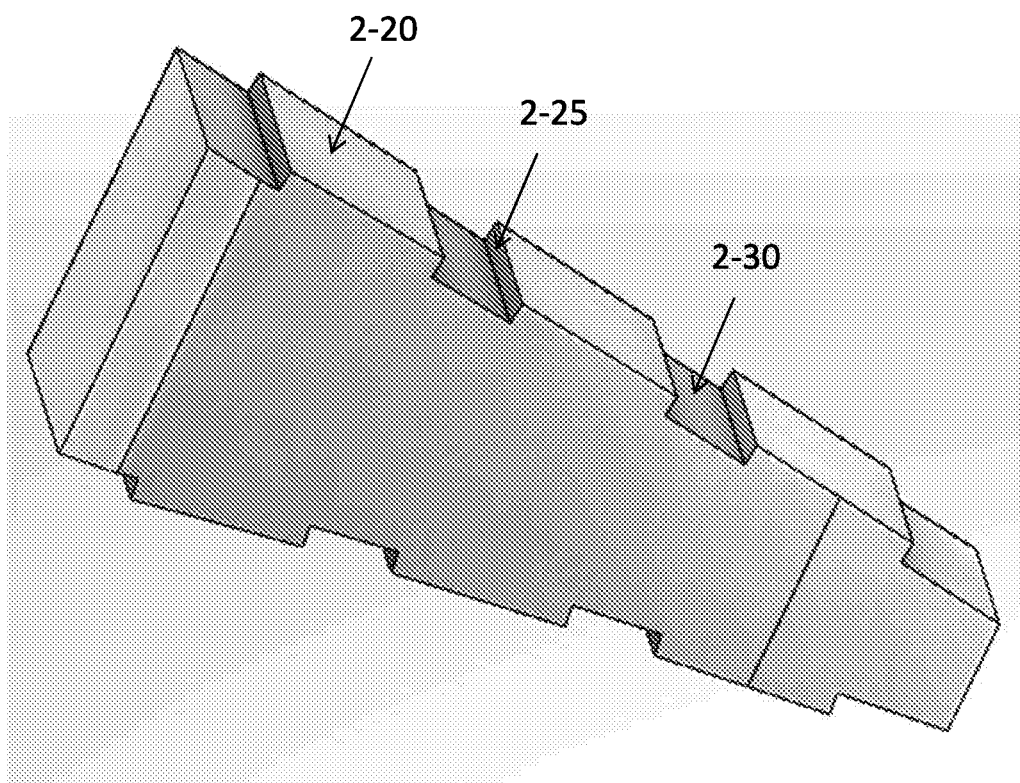

This invention provides, inter alia, a device having a cage frame having an opening or window in at least one of its frame sides that allows for the insertion of bone growth promoting materials therethrough. The fusion devices of this invention comprise one or more openings in one or more of the frame sides of the cage frame, designed to receive bone growth promoting materials, including coral-based materials, which facilitate in the fusion with the treated bone, and which optionally serves to reinforce the stability of the implanted structure.

This invention in some aspects provides a fusion device forming a rigid structure between adjoining bones comprising a cage frame defined by a top cage frame element, a bottom cage frame element and lateral cage frame elements, said cage frame elements designed to be positionable proximal to and engageable with a surface of an adjacent bone, and wherein at least one of said top and bottom cage frame elements include an opening to receive bone growth promoting materials, including coral-based materials, which facilitates in the fusion with the treated bone, and which optionally serves to reinforce the stability of the implanted structure.

In other aspects, this invention provides a fusion device forming a rigid structure to be at least partially inserted within an intervertebral disk space to form a support structure between adjoining vertebrae in a spinal column, said device comprising a cage defined by a top cage frame element, a bottom cage frame element and lateral cage frame elements, with front and back cage frame elements each having a length that is less than each length of a first and said second side cage frame elements, one of said first and second side cage frame elements extending substantially linearly along a longitudinal axis of said cage and one of said first side and said second side cage frame elements formed of a substantially uniform arcuate surface, wherein a top and bottom cage frame element is designed to be positionable between and engageable with a surface of an adjacent vertebrae, at least one of said top and bottom cage frame elements being inclined downwardly from a back end cage frame element to a front end cage frame element such that a region on or closely adjacent to said back end cage frame element has a height greater than a height of a corresponding portion of said front end cage frame element, at least one of said top and bottom cage frame elements being at least partially inclined from a second side cage frame element to a first side cage frame element such that a region on or closely adjacent to said back end cage frame element has a height greater than a height of a corresponding portion of said front end cage frame element, and at least one of a top and bottom cage frame element including an opening, at least one of said top and bottom cage frame elements including a plurality of ridges designed to engage a surface of a vertebrae and wherein at least one of said top and bottom cage frame elements include an opening to receive a bone graft promoting coral-based material, which facilitates the fusion of the vertebrae, and which optionally serves to reinforce the stability of the implanted fusion device between said adjoining vertebrae.

In some aspects the present invention provides a bone fusion device forming a rigid structure between adjoining regions in one or more bones comprising a cage frame defined by a top element, a bottom element, a front end element, a back end element, a first side element and a second side element, said top element and said bottom element designed to be positionable between, and engageable with a surface of an adjacent bone, and wherein at least one of said top and bottom elements include an opening to receive a bone growth promoting material, which facilitates the fusion of said one or more bones, and which optionally serves to reinforce the stability of the implanted fusion device between said adjoining regions in said one or more bones, wherein said bone growth promoting material is comprised of a solid block which block is machined or structurally modified to include a modified surface of the bone growth promoting material into which at least a portion of at least one cage frame element inserts seamlessly therein so that an outer face of said bone growth promoting material is neither protruding nor recessed with respect to said at least one cage frame element. In some embodiments the block machined or structurally modified to include a modified surface of the bone growth promoting material specifically is modified to contain grooves into which at least a portion of at least one cage frame element inserts seamlessly therein so that an outer face of said bone growth promoting material is neither protruding nor recessed with respect to said at least one cage frame element.

The present invention relates to a new and improved fusion device that has a load bearing structure that can support intervertebral forces further comprising a porous bone graft promoting coral-based material itself promoting bone growth provided in openings in the cage frame elements. Typically, the load bearing element/structure is made of a material that is denser than the porous matrix and can support a load in the range of at least about 8.2 kN (kilonewtons). This typically requires that the load bearing element/structure to be made of a material having a compression strength of between about 1000 MPa and 1500 MPa. In some embodiments, the bone growth promoting materials, including coral-based materials, is integrally bound to the load bearing element/structure. The fusion cage may have more than one load bearing frame element/structure. In a preferred embodiment, the fusion cage has at least two load bearing frame elements/structures.

In some aspects, the fusion device cage can be made of any biocompatible material and has a suitable size and shape for implantation into the desired site of tissue repair. In some embodiments, the load bearing wall of the fusion cage is approximately parallel to the long axis of the treated site, for example, the spinal column, when the device is inserted therein, for example, into the intervertebral space.

In others, the load bearing element/structure is angled, for example, to produce lordosis. In one embodiment, the fusion cage has a surface at each end of the load bearing element/structure which will contact the bone tissue to which the device is being affixed and the tissue/structure being adhered thereto.

Surprisingly and as exemplified herein, when the device provides a large surface area of exposed bone growth promoting material, which in some embodiments, is flush with or extends beyond the frame boundaries, thereby maximally contacting the surface of the bone whose fusion with/extravasation within is desired, then superior bone fusion and repair is stimulated.

In some aspects, the termini of the bone fusion device are intended to be in direct contact with the bone to which the device is applied, and the bone growth promoting material is flush with or extends beyond the boundaries of the cage frame. In some aspects, a different surface of the bone fusion device is intended to be in direct contact with the bone to which the device is applied, and the bone growth promoting material is flush with or extends beyond the boundaries of the cage frame such surface, for example, a lateral surface of the device.

Surprisingly and as described herein in the Examples, with regard to FIGS. 5A-5E, a bone fusion device of this invention promoted complete healing of a non-union fracture in an animal model, whereby within the non-union fracture into which the bone fusion device was placed and affixed, new bone tissue completely formed, replacing the coralline scaffold (the embodied bone growth promoting material) inside the titanium frame, and the animal fully healed from the procedure, with full motion, full weight bearing, no presence of pain, swelling or discomfort and strength restored to the animal, despite prior presence of a non-union fracture. It is noted that the titanium cage absorbed the load, enabling the brittle coralline scaffold to be incorporated into the defect and to enable complete healing with fully functional and vascularized bone. The newly functional bone is indistinguishable from native bone, The process of bone healing included initial osteo-integration of the edges of the scaffold followed by full-bone remodeling through osteo-transduction.

Surprisingly, the specific architecture of the systems of this invention allowed for the remarkable and complete healing Employing a strong care frame material, which in the Examples included the titanium frame allowed for inclusion of a solid implant that otherwise would have insufficient support to withstand the load applied thereto, therefore, the absence of the frame as included would have resulted in the collapse of the solid bone growth promoting material, in this case, the coral, and without a cage design maximizing contact between the solid bone growth promoting material and edges of the two bones to be joined, there would have been incomplete or no bone healing.

According to this aspect and in some embodiments, the device may connect between two proximal bones, for example, for treating non-union fractures, for bridging gaps or voids in a bone, arising, for example, by the presence of tumors or necrosis, or other compromising conditions in the bone. In some aspects, the device may connect between two proximal bones, for example, in sinus lift dental applications, or in fixing malalignment in bones, or for example, for treating the ribcage, or treating skull fractures, or for bridging two vertebrae to be fused together.

In another embodiment, when bridging two vertebrae to be fused together, the two surfaces that contact the vertebrae to be fused are not perpendicular to the load bearing wall, but instead are tapered in the anterior to posterior direction to achieve lordosis or in the posterior to anterior direction to achieve kyphosis.

In a preferred embodiment, the surfaces of the fusion cage may be further modified to have ridges or teeth to increase the stability of the fusion device once it is inserted into the patient.

Optionally, the fusion cage can be a series of cages stacked on top of each other, such as described in U.S. Pat. Nos. 6,195,211 and 5,192,327, the entire teachings of which are incorporated herein by reference.

Mechanical attachment of the bone growth promoting materials, including coral-based materials to the load bearing wall may be achieved by, for example, press fitting a bone growth promoting material, for example, shaped into a cylinder into a hollow sleeve, or by sintering to achieve an integral attachment.

In some aspects, the load bearing cage frame element/structure generally will have a density that is greater than the bone growth promoting material.

In some aspects, this invention provides a bone fusion device forming a rigid structure between adjoining regions in one or more bones comprising a cage frame defined by a top cage frame element, a bottom cage frame element and lateral cage frame elements, comprising a top cage frame element and a bottom cage frame element designed to be positionable between, and engageable with a surface of an adjacent bone, and wherein at least one of said top and bottom cage frame elements include an opening to receive a bone growth promoting material, including coral-based material, which facilitates the fusion of said one or more bones, and which optionally serves to reinforce the stability of the implanted fusion device between said adjoining regions in said one or more bones, wherein said bone growth promoting material, including coral-based material is comprised of a solid block machined or structurally modified to include grooves into which at least a portion of at least one cage frame element inserts seamlessly therein so that an outer face of said bone growth promoting material, including coral-based material is neither protruding nor recessed with respect to said at least one cage frame element.

In some embodiments, the device top cage frame element and bottom cage frame element are designed to be positionable between, and engageable with a surface of a bone, wherein at least one of said top and bottom cage frame elements include an opening to receive bone growth promoting materials, including coral-based materials, which facilitates the affixation to bone, or fusion of two bones, or fusion of two portions of a bone, and which optionally serves to reinforce the stability of the implanted fusion device between said adjoining structures.

In some aspects, at least one cage frame element has an arcuate portion at least partially along a longitudinal axis of said cage.

In some aspects, the cage includes a memory metal and in some aspects, the cage is adapted to form a modular component. In some aspects, the cage is adapted to be stackable with at least another cage and in some aspects the cage is adapted to receive at least one pedicle screw.

In some aspects, at least one of said top and bottom cage frame elements includes a plurality of ridges to engage a surface of an adjacent bone structure and in some embodiments the ridges are spaced from a peripheral edge of said first and second side wall.

In some embodiments, the top cage frame element, bottom cage frame element and lateral cage frame elements each have a peripheral edge, at least a portion of said peripheral edge of each of said walls being contoured so as not to be sharp.

In some embodiments, the cage frame comprises stainless steel, titanium, chrome, cobalt, polycarbonate, polypropylene, polyethylene, polymethylmethacrylate, polysulfone filled with glass or carbon fibers or a combination thereof.

In some embodiments, the bone growth promoting materials, including coral-based materials, comprises one or more solid coral pieces, or ground coral pieces or a combination thereof, which coral-based material packs within the defined area provided in the opening in said wall or walls.

In some embodiments, the bone growth promoting materials, including coral-based materials, comprises coral characterized by a specific fluid uptake capacity value of at least 75% or characterized by having a contact angle value of less than 60 degrees, when in contact with a biocompatible fluid and in some embodiments, the bone growth promoting materials, including coral-based materials, comprises coral, aragonite, calcite, mixtures thereof, or other polymorphs of the same.

In some embodiments, the bone graft promoting coral-based material is isolated from a *Porites* species, a *Goniopora*, a *Millepora* species or an *Acropora* species In some aspects, this invention provides a method for stabilizing an item to a bone, or in some embodiments, stabilizing two skeletal structures relative to one another, the method comprising: providing a bone fusion device as herein described to be disposed between the item and the bone or between the two skeletal structures, securing said bone fusion device therebetween, and in some embodiments, it is an object to inhibit movement of the skeletal structures relative to one another, even when the skeletal structures are subject to forces other than perpendicular compressive forces.

In some aspects, this invention provides a bone fusion device forming a rigid structure to be at least partially inserted within an bone disk space to form a support structure between adjoining vertebrae in a spinal column, said device comprising a cage defined by a top cage frame element, a bottom cage frame element and lateral cage frame elements, wherein a front and back end cage frame element each has a length that is less than each length of a first side and said second side cage frame element, one of said first and second side cage frame elements extending substantially linearly along a longitudinal axis of said cage and one of said first side and said second side cage frame elements formed of a substantially uniform arcuate surface, said top cage frame element and said bottom cage frame element designed to be positionable between and engageable with a surface of an adjacent vertebrae, at least one of said top and bottom cage frame elements being inclined downwardly from said back end cage frame element to said front end cage frame element such that a region on or closely adjacent to said back end cage frame element has a height greater than a height of a corresponding portion of said front end cage frame element, at least one of said top and bottom cage frame elements being at least partially inclined from said second side cage frame element to said first side cage frame element such that a region on or closely adjacent to said back end cage frame element has a height greater than a height of a corresponding portion of said front end cage frame element, at least one of said top and bottom cage frame elements including an opening, at least one of said top and bottom cage frame elements including a plurality of ridges designed to engage a surface of a vertebrae and wherein at least one of said top and bottom cage frame elements include an opening to receive a bone growth promoting material, including coral-based material, which facilitates the fusion of the vertebrae, and which optionally serves to reinforce the stability of the implanted fusion device between said adjoining vertebrae, wherein said bone graft promoting coral-based material is comprised of a solid block machined or structurally modified to include grooves into which at least a portion of at least one cage frame element inserts seamlessly therein so that an outer face of said bone growth promoting material, including coral-based material is neither protruding nor recessed with respect to said at least one cage frame element.

In some embodiments the substantially uniform arcuate surface has a radius of curvature of about 2-30° and in some embodiments, the first end cage frame element includes a substantially uniform arcuate surface or in some embodiments, the back end cage frame element has a substantially uniform planar surface. In some embodiments the top cage frame element includes said incline from said back end cage frame element to said front end cage frame element and in some embodiments, the incline is about 0.5-20°.

In some embodiments the incline of said top cage frame element from said back end cage frame element to said front end cage frame element has a substantially constant slope and in some embodiments, the bottom cage frame element includes said incline from said back end cage frame element to said front end cage frame element. In some embodiments the incline is about 0.5-20°. In some embodiments the bottom cage frame element includes said incline from said back end cage frame element to said front end cage frame element and in some embodiments, the incline of bottom cage frame element from said back end cage frame element to said front end cage frame element has a substantially constant slope. In some embodiments the top cage frame element includes said incline from said second side cage frame element to said first side cage frame element.

In some embodiments the ridges include a plurality of teeth and in some embodiments the ridges are spaced from a peripheral edge of said first and second side cage frame elements.

In some embodiments the cage frame elements each have a peripheral edge, at least a portion of said peripheral edge of a plurality of said cage frame elements being contoured so as not to be sharp.

In some embodiments the cage is able to maintain a tension load of at least about 10 pounds.

In some embodiments the at least one of said cage frame elements is adapted to be stackable with at least another prosthetic implant or in some embodiments, the at least one of said cage frame elements is adapted to be connectable to another prosthetic implant. In some embodiments the support structure is expandable.

This invention provides a method for stabilizing two skeletal structures relative to one another, the method comprising: providing a bone fusion device as described herein to be disposed between the two skeletal structures, securing said bone fusion device therebetween to inhibit movement of the skeletal structures relative to one another, even when the skeletal structures are subject to forces other than perpendicular compressive forces.

In one embodiment, the fusion cage of the invention may be made of a synthetic material, for example, in some embodiments, one that is stronger than bone, preferably, it is a sintered ceramic, such as an oxide of alumina, zirconia, titanium or a combination thereof.

In some embodiments, the bone growth promoting materials may include any solid material known in the art, for example, bone cements, bone glasses, or bone fillers or a combination thereof. In some embodiments, the bone growth promoting materials may include metal, PLGA, PGA, any appropriate carbon composite implant material, ceramic material, alginate-based implant, and others, as will be appreciated by the skilled artisan, which when implanted in situ as part of the fusion devices as described herein, is of sufficient strength and hardness and useful in stimulating bone repair In some embodiments, the bone cements may include any known cement, including β-Tricalcium phosphate, Monocalcium phosphate monohydrate (MCPM) (Ca(H$_2$PO$_4$) 2H$_2$O) and mixtures thereof, including Brucite cement. In some embodiments, the cement may include amorphous calcium phosphate (ACP), dicalcium phosphate dihydrate (DCPD), dicalcium phosphate anhydrous (DCPA), β-tricalcium phosphate (β-TCP), dicalcium phosphate (DCP), tetracalcium phosphate (TTCP), monocalcium phosphate monohydrate (MCPM), calcium carbonate (CC) and others, and mixtures thereof.

In ceramic materials, the pore size can be controlled by conventional techniques, such as controlling the temperature during the sintering process. Ceramic sintering techniques are known to those skilled in the art. In a preferred embodiment, the ceramic includes an osteoconductive material, such as hydroxyapatite or tricalcium phosphate, to promote bone growth into the fusion device. In one embodiment, the osteoconductive material may be added as a coating on the inner surface of the porous matrix.

Other suitable materials for the fusion cage include biopolymers such as, for example, polylactic acid, polyglycolic acid, a copolymer of polylactic acid and polyglycolic acid, a polyarylethyl ketone, polygalactic acid, polycaprolactone, polyethylene oxide, polypropylene oxide, polysulfone, polyethylene, polypropylene, a polyaryletherketone, and combinations thereof. In one embodiment, the fusion cage comprises a polyaryletherketone. In a preferred embodiment, the percentage of the fusion cage that is a polyaryletherketone is in the range of between about 40 vol % and about 90 vol %. In another embodiment, the polyaryletherketone is mixed with carbon fibers which are typically chopped. In a preferred embodiment, the percentage of the fusion cage that is carbon fiber is in the range of between about 1 vol % and about 60 vol %. Examples of polyaryletherketones include polyetheretherketone, poly(arylether ketone ketone), and polyetherketone.

The bone growth promoting materials, including coral-based materials, may be attached to the inner surface of the cage. Such bone growth promoting materials, including coral-based materials, may further comprise additional therapeutic additives to further stimulate integration of the fusion device, such as progenitor cells, growth factors, and others.

In some aspects, the term "progenitor cells," as used herein, refers to cells that are capable of differentiating into bone. Examples of progenitor cells include mesenchymal stem cells, hematopoietc cells, and embryonic stem cells. In one embodiment, progenitor cells are attached to the inner surface of the porous matrix by passing bone marrow aspirate suspension through the fusion cage.

In some aspects, the term "growth factors" as used herein encompasses any cellular product that modulates the growth or differentiation of other cells, particularly connective tissue progenitor cells. Growth factors include, but are not limited to, isoforms of platelet derived growth factors (PDGF), fibroblast growth factors, epithelial growth factors, isoforms of transforming growth factor Beta, insulin-like growth factors, bone morphogenic proteins and precursors thereof.

In some aspects, the bone growth promoting materials, including coral-based materials, may be pre-soaked or pre-seeded with progenitor cells, growth factors, or other therapeutic agents prior to their incorporation within the fusion devices of this invention.

In some embodiments, the growth factors may include, for example, isoforms of platelet derived growth factors, fibroblast growth factors, epithelial growth factors, transforming growth factor Beta, insulin-like growth factor(s), parathyroid hormone (PTH) or PTH related peptide, and bone morphogenic proteins and precursors thereof.

The bone growth promoting materials, including coral-based materials, is in some aspects, characterized by a specific fluid uptake capacity value of at least 75% or is characterized by having a contact angle value of less than 60 degrees, when in contact with a fluid.

The bone growth promoting materials, including coral-based materials of this invention are characterized by a specific fluid uptake capacity value of at least 75%, which specific fluid uptake capacity value is determined by establishing a spontaneous fluid uptake value divided by a total fluid uptake value, or are characterized by having a contact angle value of less than 60 degrees, when in contact with a fluid. Methods for the determination of the specific fluid uptake and contact angle value have been described, for example, in PCT International Application Publication Number WO2014125478, hereby incorporated by reference in its entirety.

Coral, which is comprised of $CaCO_3$ in the crystalline form of aragonite or calcite has been shown to possess the advantage of supporting fast cellular invasion, adherence and proliferation. Coral has been shown to be an effective substrate for facilitation of the adherence, proliferation and differentiation of mesenchymal stem cells, and ultimate incorporation into cartilage and/or bone tissue. Coral has also been shown to serve as an excellent substrate for promoting adherence and proliferation of a number of other cell types, serving as an excellent support for cell and tissue growth.

The terms "coral" and "aragonite" and "calcite" may be used interchangeably herein.

In one embodiment, "the bone growth promoting materials, including coral-based materials" refers to a shaped platform used in the fusion devices of this invention, wherein the bone growth promoting materials, including coral-based material provides a site for repair and/or restored function in the implanted site. In one embodiment, the bone growth promoting materials, including coral-based materials is a temporary platform. In one embodiment, "temporary platform" refers to a natural degradation of the material that occurs over time during such repair, wherein the natural fully or partially degradation of the material may result in a change of shape over time and/or change in size over time, ultimately positively impacting healing/promoting greater functionality at the implanted site.

It will be appreciated that different bone growth promoting materials, including coral-based materials, may include optionally pores, which in turn optionally vary in terms of their average pore diameter and pore volume and the invention contemplates use of any such starting material for the preparation of the bone growth promoting materials as herein described, where the solid substrate is characterized in that it is characterized by a specific fluid uptake capacity value of at least 75%.

As used herein, the term "pore volume" refers to volume or open spaces inside the porous scaffolding of this invention. Pore volume is determined by any means known in the art. Porosity can be calculated by standard methods, an example of which is provided further hereinbelow, see for example, Karageorgiou V, Kaplan D. (2005) "Porosity of 3D biomaterial scaffolds and osteogenesis" Biomaterials; 26(27):5474-91, which is hereby incorporated by reference in its entirety.

In one embodiment, the fusion devices of this invention employ use of a coral, including, inter alia, *Porites, Acropora, Goniopora, Millepora*, or a combination thereof.

In one embodiment, the coral is from the *Porites* species. In one embodiment, the coral is *Porites Lutea*. In one embodiment, the coral is from the *Acropora* species. In one embodiment, the coral is *Acropora grandis*, which in one embodiment is very common, fast growing, and easy to grow in culture. Thus, in one embodiment *Acropora* samples can be easily collected in sheltered areas of the coral reefs and collection from the coral reefs can be avoided by use of cultured coral material.

In another embodiment, the coral is from the *Millepora* species. In one embodiment, the coral is *Millepora dichotoma*. In one embodiment, the coral has a pore size of 150 μm and can be cloned and cultured, making Millerpora useful as a framework in the solid substrates, methods and/or kits of this invention.

In one embodiment, the coral is from the *Goniopora* species. In some embodiments, the coral is *Goniopora albiconus, Goniopora burgosi, Goniopora cellulosa, Goniopora ceylon, Goniopora ciliatus, Goniopora columna, Goniopora djiboutiensis, Goniopora eclipsensis, Goniopora fruticosa, Goniopora gracilis, Goniopora klunzingeri, Goniopora lobata, Goniopora mauritiensis, Goniopora minor, Goniopora norfolkensis, Goniopora palmensis, Goniopora pandoraensis, Goniopora parvistella, Goniopora pearsoni, Goniopora pendulus, Goniopora planulata, Goniopora polyformis, Goniopora reptans, Goniopora savignyi, Goniopora somaliensis, Goniopora stokes, Goniopora stutchburyi, Goniopora sultani, Goniopora tenella, Goniopora tenuidens* or *Goniopora viridis*.

In another embodiment, the coral is from any one or more of the following species *Favites halicora; Goniastrea retiformis; Acanthastrea echinata; Acanthastrea hemprichi; Acanthastrea ishigakiensis; Acropora aspera; Acropora austera; Acropora* sp. "brown digitate"; *Acropora carduus; Acropora cerealis; Acropora chesterfieldensis; Acropora clathrata; Acropora cophodactyla; Acropora* sp. "danai-like"; *Acropora divaricata; Acropora donei; Acropora echinata; Acropora efflorescens; Acropora gemmifera; Acropora globiceps; Acropora granulosa; Acropora cf hemprichi; Acropora kosurini; Acropora cf loisettae; Acropora longicyathus; Acropora loripes; Acropora cf lutkeni; Acropora paniculata; Acropora proximalis; Acropora rudis; Acropora selago; Acropora solitaryensis; Acropora cf spicifera* as per Veron; *Acropora cf spicifera* as per Wallace; *Acropora tenuis; Acropora valenciennesi; Acropora vaughani; Acropora vermiculata; Astreopora gracilis; Astreopora myriophthalma; Astreopora randalli; Astreopora suggesta; Australomussa rowleyensis; Coscinaraea columna; Coscinaraea crassa; Cynarina lacrymalis; Distichopora violacea; Echinophyllia echinata; Echinophyllia cf echinoporoides; Echinopora gemmacea; Echinopora hirsutissima; Euphyllia ancora; Euphyllia divisa; Euphyllia yaeyamensis; Favia rotundata; Favia truncatus; Favites acuticollis; Favities pentagona; Fungia granulosa; Fungia klunzingeri; Fungia mollucensis; Galaxea acrhelia; Goniastrea edwardsi; Goniastea minuta; Hydnophora pilosa; Leptoseris explanata; Leptoseris incrustans; Leptoseris mycetoseroides; Leptoseris scabra; Leptoseris yabei; Lithophyllon undulatum; Lobophyllia hemprichii; Merulina scabricula; Millepora dichotoma; Millepora exaesa; Millipora intricata; Millepora murrayensis; Millipora platyphylla; Monastrea curta; Monastrea colemani; Montipora caliculata; Montipora capitata; Montipora foveolata; Montipora meandrina; Montipora tuberculosa; Montipora cf vietnamensis; Oulophyllia laevis; Oxypora crassispinosa; Oxypora lacera; Pavona bipartita; Pavona venosa; Pectinia*

*alcicornis; Pectinia paeonea; Platygyra acuta; Platygyra pini; Platygyra* sp "green"; *Platygyra verweyi; Podabacia cf lanakensis; Porites annae; Porites cylindrica; Porites evermanni; Porites monticulosa; Psammocora digitata; Psammocora explanulata; Psammocora haimeana; Psammocora superficialis; Sandalolitha dentata; Seriatopora caliendrum; Stylocoeniella armata; Stylocoeniella guentheri; Stylaster* sp.; *Tubipora musica; Turbinaria stellulata*; or any coral known in the art, or a combination thereof.

In some embodiments, coral for use in the devices and/or methods of this invention may comprise scleractinian coral, including in some embodiments, *Goniopora* and others. In some embodiments, coral for use in the devices and/or methods of this invention may comprise Alveoppora. In some embodiments, coral for use in the devices and/or methods of this invention may comprise a natural bone mimetic material such as bamboo, corals, including in some embodiments, coral from the family Isididae, genera Keratoisis, Isidella, and others.

In one embodiment of this invention, the term "coral" refers to coral which is cut from a single piece of coral.

In one embodiment, the bone growth promoting materials, including coral-based materials, may be machined into desired configurations, and quite complex shapes may be prepared, e.g. being further modified to include or be shaped to include a threaded structure is envisioned and the same may be formed by appropriate machine or other processing, such as chemical processing.

In some embodiments, the bone growth promoting material, including coral-based materials is scaled into a size/dimension so as to be most approximate to accommodate a site of desired implantation.

In some embodiments, the bone growth promoting materials, including coral-based materials, comprises a specifically introduced non-native hollow or hollows along a Cartesian coordinate axis of said bone growth promoting material for use in the devices and/or methods of this invention.

In one embodiment, the size of the bone growth promoting material, including coral-based material, may be any size and/or any shape that would be useful for the purposes of the present invention, as would be known to one of skill in the Art depending on the purpose.

For example and in one embodiment, the bone growth promoting materials, including coral-based materials, may be substantially the same size as the surface of adjacent vertebrae, intended to be in contact with said coral, while in another embodiment, the solid substrate or a portion thereof may be smaller in size than the surface of adjacent vertebrae, intended to be in contact with said coral.

In one embodiment, bone growth promoting materials, including coral-based materials, for use in a devices and/or methods of this invention comprises an average void diameter, average pore size or a combination thereof appropriate for cell seeding and/or development of bone remodeling and/or repair.

In one embodiment, coral is washed, bleached, frozen, dried, exposed to electrical forces, magnetic forces or ultrasound waves or microwaves or electromagnetic radiation or high pressure or a combination thereof prior to use thereof.

It will be appreciated by the skilled artisan that the overall shape of the coral and in some embodiments, the cage and in some embodiments, the intervertebral fusion device may be so selected so as to be suitable to the desired application. Accordingly, this invention is not to be limited by the shape of the coral and/or in some embodiments, the cage and/or in some embodiments, the fusion devices of this invention.

In some embodiments, the coral for use in accordance with the instant invention may be prepared as described in PCT International Application publication Number WO 2009/066283, PCT International Application publication Number WO 2010/058400, PCT International Application publication Number WO 2010/146574 and PCT International Application publication Number WO 2010/146574, each of which is fully incorporated by reference herein, in its entirety.

Bone growth promoting materials, including coral-based materials of this invention are characterized by a specific fluid uptake capacity value as desired for the specific application for example of at least 75%, which specific fluid uptake capacity value is determined by establishing a spontaneous fluid uptake value divided by a total fluid uptake value.

In some embodiments, the fluid is a biologic fluid, which in some embodiments is blood, and in some embodiments, the biologic fluid is water. In some embodiments, the biologic fluid is hydrophilic. In some embodiments the fluid is a plasma or plasma-containing solution. In some embodiments, the fluid is a protein-containing or carbohydrate-containing solution. In some embodiments the fluid is a salt-containing solution. In some embodiments, the solution is a glycoprotein-containing solution.

In some embodiments, the biologic fluid is autologous with respect to a cell or tissue of a subject when said bone graft promoting coral-based material is contacted with such cell or tissue of said subject.

In some embodiments, the biologic fluid is a blood analog as herein defined.

In some embodiments, surprisingly, it was found that a solution containing 40% glycerol and 1 g/L glucose in normal saline was a useful fluid for evaluation of the specific fluid uptake capacity values of the solid substrates as herein described. In some embodiments, such solution is referred to as a "blood analogue" as its biocompatibility and other desirable characteristics, such as viscosity for the purpose of evaluating the specific fluid uptake capacity values of the solid substrates as herein described provides values as consistently as when autologous or allogeneic blood is used, or water and therefore can serve as an analogue for such screening protocols.

In some aspects, reference to a blood analogue herein will be understood to specifically refer to any solution containing from about 20 to about 60% glycerol and 1 g/L glucose in normal saline.

In some aspects, such blood analogue may further comprise a color indicator or dye, such as 1-D&C blue #2 Aluminum lake dye or FD&C blue #2 dye, or any other appropriate color indicator, as will be appreciated by the skilled artisan. In some embodiments, the blood analogue will comprise 1 g/L 1-D&C blue #2 Aluminum lake dye, or in some embodiments, the blood analogue will further comprise 0.075 g/L FD&C blue #2 dye, as these are convenient concentrations for the color indicator. It will be appreciated by the skilled artisan that the color indicator may be provided at any convenient concentration that provides a desired detectable signal.

It will be appreciated by the skilled artisan that the fluid for use in determining specific fluid uptake capacity values of the bone graft promoting coral-based material as herein described may include any appropriate described fluid, for example, Salt based solutions such as physiologic Saline (0.9% NaCl), or in some embodiments, Carbohydrate based solutions such as Glucose 1 g/L in saline, or in some embodiments, Glucose 1 g/L in WFI, or in some embodiments, Glucose 10 g/L in WFI, or in some embodiments, a Protein based solution such as BSA 50 g/L in saline, or in some embodiments, BSA 5 g/L in in WFI, or in some embodiments, BSA 0.5 g/L in in WFI, or in some embodiments, a Glycerol based solution, such as, for example, 22% Glycerol in saline, or in some embodiments, 22% Glycerol in WFI, or in some embodiments, 30% Glycerol in WFI, or in some embodiments, 44% Glycerol in WFI, or in some embodiments, a Xanthan-Gum & Glycerol solution, such as, for example, 0.025% Xanthan-Gum+30% Glycerol in WFI, or in some embodiments, combinations of the above, for example, Glycerol/Glucose/BSA/saline/Skim milk, or in some embodiments, Glucose 0.1 g/dL+BSA 5 g/dL in saline, or in some embodiments, 5 g/dL skim milk in saline, or in some embodiments, 22% Glycerol+50 g/L skim milk in saline, or in some embodiments, 22% Glycerol+10 g/L Glucose in saline, or in some embodiments, 22% Glycerol+1 g/L Glucose in saline, or in some embodiments, 30% Glycerol+1 g/L Glucose in saline, or in some embodiments, 30% Glycerol+10 g/L Glucose in saline, or in some embodiments, 32.5% Glycerol+1 g/L Glucose in saline, or in some embodiments, 35% glycerol+1 g/L Glucose in saline, or in some embodiments, 35% Glycerol+1 g/L Glucose in saline, or in some embodiments, 40% Glycerol+1 g/L Glucose in saline, or in some embodiments, PEG/Tween 20/Gelatin such as, for example, 40% Glycerol+1 g/L Glucose in saline+1% PEG, or in some embodiments, 40% Glycerol+1 g/L Glucose in saline+0.1% PEG, or in some embodiments, 40% Glycerol+1 g/L Glucose in saline+0.1% PEG+0.1% Tween 20, or in some embodiments, 40% Glycerol+1 g/L Glucose in saline+0.1% PEG+0.1% Gelatin, and others, as will be appreciated by the skilled artisan.

It will also be appreciated by the skilled artisan that any such fluid for use in determining the specific fluid uptake capacity values of the bone graft promoting coral-based material as herein described may also be considered to represent an envisioned "blood analogue" as herein described.

It will be understood that any of the above are considered for use in determining the specific fluid uptake capacity values of the bone graft promoting coral-based material as herein described and may in part function as a type of blood analogue for the purpose of such determination. In some aspects, as a preferred embodiment of a blood analogue as referred to herein, such analogue will comprise 40% glycerol and 1 g/L glucose in normal saline and optionally will further comprise a color indicator as herein described.

In some aspects, the blood analog as herein described will be further characterized by the following characteristics: having a density of approximately 1.12 g/mL; and having a viscosity of approximately 4.57 mPa/sec at 25° C.

It will be understood that the biologic fluid may be any fluid which is biocompatible and whose incorporation is appropriate within a bone graft promoting coral-based material for the desired application.

In some embodiments, the process further comprises the step of contacting the material with a fluid for from 2-15 minutes to promote spontaneous fluid uptake of said fluid within said bone graft promoting coral-based material to arrive at said spontaneous fluid uptake value. In some embodiments, the process may allow for the contacting of the material with a fluid for from 0.5-15 minutes, or in some embodiments, from 0.5-5 minutes, or in some embodiments, 10-60 minutes, or in some embodiments, from 60 to 90 minutes, or in some embodiments, other intervals, to promote spontaneous fluid uptake. The skilled artisan will appreciate that the amount of time for which the fluid is applied to determine the spontaneous uptake may be extended or shortened as a function of the dimensions and geometry of the sample substrate being assessed. In some embodiments, when a larger sample is being assessed, the process further comprises the step of contacting the material with a fluid for from 2-24 hours to promote spontaneous fluid uptake of said fluid within said bone graft promoting coral-based material to arrive at said spontaneous fluid uptake value In some embodiments, the process further comprises the step of contacting said bone growth promoting materials, including coral-based materials, with a fluid and applying negative pressure to the bone growth promoting materials to promote maximal uptake of said fluid within said bone growth promoting materials, to arrive at said total fluid uptake value. In some embodiments, application of positive pressure is via the application of a vacuum to the substrate immersed in the fluid, promoting entry of the fluid therewithin.

In some embodiments, the process may further comprise the step of contacting the bone growth promoting materials, including coral-based materials, with a fluid and applying positive pressure to same to promote maximal uptake of fluid within the bone growth promoting materials to arrive at said total fluid uptake value. According to this aspect, and in some embodiments, care will be taken to ensure that the application of pressure does not in any way compromise the structural integrity of the bone growth promoting materials.

In some embodiments, application of positive pressure is via any manual means, for example, via the use of any applicator, syringe, etc., gravitational pressure, and others, as will be appreciated by the skilled artisan. In some embodiments, application of positive pressure is via forced osmosis, centrifugation and others. In some embodiments, combinations of the described methods and others are envisioned.

In some embodiments, the bone growth promoting material comprises a coralline or coralline derivative characterized by having a contact angle value of less than 60 degrees, when in contact with a fluid.

Methods for determining a contact angle are well known, and any appropriate method can be used.

In some aspects, the sample is further dried under vacuum and/or heated or pressurized or steam treated.

In some embodiments, for aspects relating to a specific fluid uptake capacity value, such value is a function of change in weight in the bone graft promoting coral-based material.

In some aspects, the bone growth promoting material, including coral-based material is cut from a given larger sample assessed to ensure same conforms to the stated specific fluid uptake capacity value of at least 75% or contact angle value of less than 60 degrees, when in contact with a biocompatible fluid as determined in the larger sample, thereby ensuring that the bone graft promoting coral-based material is similarly characterized by the stated specific fluid uptake capacity value of at least 75% or contact angle value of less than 60 degrees, when in contact with a biocompatible fluid.

According to this aspect and in some embodiments, the dry weight for each sample is recorded and fluid as described herein is added an assay container.

According to this aspect and in some embodiments, at least 1:1 ratio of the size of the sample in mm to the volume of fluid added in ml is applied to the container. In some embodiments, the amount of fluid applied is in excess, as compared to the sample size.

According to this aspect and in some embodiments, once the initial fluid uptake is assessed, according to this aspect and in some embodiments, the bone growth promoting materials, including coral-based materials, is then brought into contact with the fluid and the weight of the bone growth promoting material is assessed. In other embodiments the specific gravity is assessed by gradient centrifugation of by the Archimedean principle.

According to this aspect and in some embodiments, spontaneous fluid uptake is assessed and a spontaneous fluid uptake value is established, based on the change in weight of the bone growth promoting material.

According to this aspect and in some embodiments, the specific fluid uptake capacity value is a function of change in fluid volume of applied fluid to said bone growth promoting material. According to this aspect, spontaneous fluid uptake is assessed and a spontaneous fluid uptake value is established based on the complete uptake of the volume applied to the sample.

According to this aspect and in some embodiments, the process then further comprises contacting a significantly increased amount of fluid with the sample and applying pressure thereto to promote maximal fluid uptake to the total fluid uptake capacity of the sample.

According to this aspect and in some embodiments, as noted, such pressure may be either positive or negative pressure, and the application time is for a period of time sufficient to ensure maximal uptake of the applied fluid to the sample.

According to this aspect and in some embodiments, such time may include an interval of from 0.5-60 minutes, or in some embodiments, when a larger sample is being assessed, such time may include an interval of from 2-24 hours to arrive at said spontaneous fluid uptake value. It will be appreciated that the time intervals recited herein are applicable for any embodiment with regard thereto as described herein. The skilled artisan will appreciate that the amount of time for which the fluid is applied to determine the full capacity fluid uptake may be extended or shortened as a function of the dimensions and geometry of the sample being assessed.

According to these aspects, the total fluid uptake capacity is thus assessed and the specific fluid uptake capacity value is then determined.

In some embodiments, the invention specifically contemplates bone growth promoting materials having a specific fluid uptake capacity value exceeding the cutoff value of 75%, for the sample to be optimized for the described methods and/or devices of this invention. It will be appreciated that the invention contemplates the stated cutoff value for promoting a reasonable value that reduces the presence of appreciable false positives, i.e. bone growth promoting materials that are not as optimal for the stated applications.

In some embodiments, samples thus processed and found to be characterized by a specific fluid uptake capacity value of at least 75%, or specific selection of bone growth promoting materials characterized by having a contact angle value of less than 60 degrees, when in contact with a fluid may then be used for the isolation of proximally located regions of a section from which such sample was taken, which samples can then be reliably used and considered as being optimized in accordance with the processes of this invention. In some embodiments, with regard to coral-based samples, such regions may include the entire annual growth ring region within the coral from which the sample was derived.

In some embodiments, samples thus processed and found to be characterized by a specific fluid uptake capacity value of at least 75%, or specific selection of bone graft promoting coral-based materials characterized by having a contact angle value of less than 60 degrees, when in contact with a fluid, may then be dried fully and utilized for implantation into a subject as described herein.

In some embodiments, when the sample is utilized in vivo in subsequent applications, in some aspects, the sample is first contacted with autologous biological fluids or materials from the host prior to implantation into the same, verifying the observed enhanced fluid uptake phenotype as herein described.

In one embodiment of this invention, the bone growth promoting materials may further comprise an additional material.

In some embodiments, such additional material may include a polymer.

The term "polymer" refers, in some embodiments, to the presence of a layer of polymeric material in association with at least a portion of the bone growth promoting material. In some embodiments, such polymer layer is a coating for the solid substrate material.

In some embodiments, such coating may be over the entirety of the bone growth promoting material, and in some embodiments, such coating may penetrate to within voids and/or pores and/or hollows of the material. In some embodiments, such coating may be selectively applied to a particular region of the bone growth promoting material, such that it creates a separate phase on the material, and in some embodiments, such polymer may be so applied that a thick polymer layer or phase is associated with a portion of a bone growth promoting material, thereby creating a separate polymer phase in association with the material as herein described.

In one embodiment, the polymer coating provides added features to the bone growth promoting material as herein described, for example, added tensile strength, added flexibility, reduced brittleness, and other attributes, to the bone graft promoting coral-based material and in some embodiments, the polymer coating results in greater cellular attraction and attachment to the bone growth promoting materials as herein described, which in turn, inter alia, results in enhanced repair in terms of quantity, quality and timing of repair. In some embodiments, the polymer coating enhance cells proliferation and/or differentiation into desired mature tissue which in turn, inter alia, results in enhanced repair in terms of quantity, quality and timing of repair.

In one embodiment of this invention, a polymer coating is permeable. In one embodiment, the permeable polymer coating comprises a special porous membrane. In one embodiment, the term "permeable" refers to having pores and openings. In one embodiment, the permeable polymer coating of this invention has pores and openings which allow entry of nutrients, a therapeutic compound, a cell population, a chelator, or a combination thereof. In one embodiment, the permeable polymer coating of this invention has pores and openings which allow exit/release of nutrients, a therapeutic compound, a cell population, a chelator, or a combination thereof.

In one embodiment, a polymer coating of this invention is discontinuous. In one embodiment, a region or a plurality of sub-regions of the coral of this invention comprise an absence of polymer coating, allowing direct contact between the coral and the environment.

In some embodiments, the bone growth promoting material incorporates a biocompatible polymer therewithin, which is associated with the backbone component, via any physical or chemical association. In some embodiments, the polymer is a part of a hydrogel, which is incorporated in the bone growth promoting materials of this invention. In some embodiments, such hydrogel-containing bone growth promoting materials may thereafter be lyophilized or dessicated, and may thereafter be reconstituted.

In some embodiments of the bone growth promoting materials of this invention, the polymer may be applied to the bone growth promoting material so as to form a separate phase, or in some embodiments, the polymer may be applied as a layer onto the material, or in some embodiments, the bone growth promoting material may comprise both polymer as an internal or externally associated layer with a separate phase attached thereto comprising the same or a different polymeric material.

In one embodiment, a polymer coating of this invention comprises a natural polymer comprising, collagen, fibrin, elastin, silk, hyaluronic acid, sodium hyaluronate, cross linked hyalronic acid, chitosan, cross linked chitosan, alginate, calcium alginate, cross linked calcium alginate and any combinations thereof.

In one embodiment, the polymer comprises synthetically modified natural polymers, and may include cellulose derivatives such as alkyl celluloses, hydroxyalkyl celluloses, cellulose ethers, cellulose esters and nitrocelluloses. Examples of suitable cellulose derivatives include methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate and cellulose sulfate sodium salt.

In one embodiment, of this invention, a polymer comprises a synthetic biodegradable polymer. In one embodiment of this invention, a synthetic biodegradable polymer comprises alpha-hydroxy acids including poly-lactic acid, polyglycolic acid, enantioners thereof, co-polymers thereof, polyorthoesters, and combinations thereof.

In one embodiment, a polymer of this invention comprises a poly(cianoacrylate), poly(alkyl-cianoacrylate), poly (ketal), poly(caprolactone), poly(acetal), poly(α-hydroxy-ester), poly(α-hydroxy-ester), poly(hydroxyl-alkanoate), poly(propylene-fumarate), poly (imino-carbonate), poly(ester), poly(ethers), poly(carbonates), poly(amide), poly(siloxane), poly(silane), poly(sulfide), poly(imides), poly(urea), poly(amide-enamine), poly(organic acid), poly(electrolytes), poly(p-dioxanone), poly(olefin), poloxamer, inorganic or organomatallic polymers, elastomer, or any of their derivatives, or a copolymer obtained by a combination thereof.

In one embodiment, a polymer of this invention comprises poly(D,L-lactide-co-glycolide) (PLGA). In another embodiment, the polymer comprises poly(D,L-lactide) (PLA). In another embodiment, the polymer comprises poly(D,L-glycolide) (PGA). In one embodiment, the polymer comprises a glycosaminoglycan.

In one embodiment, the polymer comprises synthetic degradable polymers, which may include, but are not limited to polyhydroxy acids, such as poly(lactide)s, poly(glycolide)s and copolymers thereof; poly(ethylene terephthalate); poly(hydroxybutyric acid); poly(hydroxyvaleric acid); poly[lactide-co-(ε-caprolactone)]; poly[glycolide-co(ε-caprolactone)]; poly(carbonate)s, poly(pseudo amino acids); poly(amino acids); poly(hydroxyalkanoate)s; poly(anhydrides); poly(ortho ester)s; and blends and copolymers thereof.

In one embodiment of this invention, a polymer comprises proteins such as zein, modified zein, casein, gelatin, gluten, serum albumin, collagen, actin, α-fetoprotein, globulin, macroglobulin, cohesin, laminin, fibronectin, fibrinogen, osteocalcin, osteopontin, osteoprotegerin, or others, as will be appreciated by one skilled in the art. In another embodiment, a polymer may comprise cyclic sugars, cyclodextrins, synthetic derivatives of cyclodextrins, glycolipids, glycosaminoglycans, oligosaccharide, polysaccharides such as alginate, carrageenan (χ, λ, μ, κ), chitosane, celluloses, condroitin sulfate, curdlan, dextrans, elsinan, furcellran, galactomannan, gellan, glycogen, arabic gum, hemicellulose, inulin, karaya gum, levan, pectin, pollulan, pullulane, prophyran, scleroglucan, starch, tragacanth gum, welan, xanthan, xylan, xyloglucan, hyaluronic acid, chitin, or a poly(3-hydroxyalkanoate)s, such as poly(β-hydroxybutyrate), poly(3-hydroxyoctanoate) or poly(3-hydroxyfatty acids), or any combination thereof.

In one embodiment, the polymer comprises a bioerodible polymer such as poly(lactide-co-glycolide)s, poly(anhydride)s, and poly(orthoester)s, which have carboxylic groups exposed on the external surface as the smooth surface of the polymer erodes, which may also be used. In one embodiment, the polymer contains labile bonds, such as polyanhydrides and polyesters.

In one embodiment, a polymer may comprise chemical derivatives thereof (substitutions, additions, and elimination of chemical groups, for example, alkyl, alkylene, hydroxylations, oxidations, and other modifications routinely made by those skilled in the art), blends of, e.g. proteins or carbohydrates alone or in combination with synthetic polymers.

In one embodiment of this invention, the polymer is biodegradable. In one embodiment, the term "biodegradable" or grammatical forms thereof, refers to a material of this invention, which is degraded in the biological environment of the subject in which it is found. In one embodiment, the biodegradable material undergoes degradation, during which, acidic products, or in another embodiment, basic products are released. In one embodiment, bio-degradation involves the degradation of a material into its component subunits, via, for example, digestion, by a biochemical process. In one embodiment, biodegradation may involve cleavage of bonds (whether covalent or otherwise), for example in a polymer backbone of this invention. In another embodiment, biodegradation may involve cleavage of a bond (whether covalent or otherwise) internal to a side-chain or one that connects a side chain to, for example a polymer backbone.

In one embodiment, a bone growth promoting material of this invention is covalently associated with the polymer coating via the use of a cross-linking agent. In one embodiment, the phrase "cross-linking agent" refers to an agent which facilitates the formation of a covalent bond between 2 atoms. In one embodiment, the cross-linking agent is a zero-length cross-linking agent.

In one embodiment, the cross-linking agent is (1 ethyl 3-(3dimethyl aminopropyl)carbodiimide (EDAC), N-Sulfohydroxy succinamide (Sulfo NHS), 5-iodopyrimidines, N-carbalkoxydihydroquinolines, pyrroloquinolinequinones, genipin or a combination thereof.

In one embodiment, the cross-linking agent is a homobifunctional cross-linker, such as, for example, a N-hydroxysuccinimide ester (e.g. disuccinimidyl suberate or dithiobis (succinimidylpropionate), homobifunctional imidoester (e.g. dimethyladipimidate or dimethyl pimelimidate), sulfhydryl-reactive crosslinker (e.g. 1,4-di-[3'-(2'-pyridyldithio)

propionamido]butane), difluorobenzene derivative (e.g. 1,5-difluoro-2,4-dinitrobenzene), aldehyde (e.g. formaldehyde, glutaraldehyde), bis-epoxide (e.g. 1,4-butanediol diglycidyl ether), hydrazide (e.g. adipic acid dihydrazide), bis-diazonium derivative (e.g. o-tolidine), bis-alkylhalide, or a combination thereof.

In one embodiment, the cross-linking agent is a hetero-bifunctional cross-linker, such as, for example, an amine-reactive and sulfhydryl-reactive crosslinker (e.g. N-succinimidyl 3-(2-pyridyldithio)propionate, a carbonyl-reactive and sulfhydryl-reactive crosslinker (e.g. 4-(4-N-maleimidophenyl)butyric acid hydrazide), or a combination thereof.

In some embodiments, the cross-linking agent is a tri-functional cross-linkers, such as, for example, 4-azido-2-nitrophenylbiocytin-4-nitrophenyl ester, sulfosuccinimidyl-2-[6-biotinamido]-2-(p-azidobenzamido)hexanoamido]ethyl-1,3'-dithiopropionate (sulfo-SBED), or a combination thereof.

In another embodiment, the cross-linking agent is an enzyme. In one embodiment of this invention, the cross-linking agent comprises a transglutaminase, a peroxidase, a xanthine oxidase, a polymerase, or a ligase, or a combination thereof.

The choice of concentration of the cross-linking agent utilized for activity will vary, as a function of the volume, agent and polymer chosen, in a given application, as will be appreciated by one skilled in the art.

In one embodiment, the association of a bone growth promoting material of this invention with a polymer coating of this invention comprises a physical and/or mechanical association. For example, in one embodiment, a physical and/or mechanical association may comprise imbibing of any means, air drying, using a cross-linking agent, applying of heat, applying vacuum, applying lyophilizing methods, freezing, applying mechanical forces or any combination thereof, to promote the physical association between a coral and a polymer coating as described herein.

In some embodiments, the choice of polymer, or application of polymer to a bone growth promoting material as herein described may be so chosen, for an added ability to increase fluid uptake. Similarly, the surface of the bone graft promoting coral-based material may be treated to increase fluid uptake therewithin, as well. In some embodiments, such surface treatment may include application of plasma to the bone graft promoting coral-based material.

It will be apparent to one skilled in the art that the physical and/or chemical properties of a polymer application to a bone growth promoting material of this invention and components thereof may influence the devices and/or methods of use of this invention in terms of the extent/quality of treatment.

In one embodiment, the polymer as applied to the bone growth promoting materials of this invention has a thickness of between 2.0 µm and 0.1 µm. In one embodiment, the polymer coating has a thickness of about 1.0 µm. In one embodiment, the polymer coating of this invention has a thickness of between 10 µm and 50 µm. In one embodiment, the polymer coating as applied to the solid substrates of this invention has a thickness of about 10-25, or about 15-30, or about 25-50 µm. In one embodiment, the polymer coating as applied to the solid substrates of this invention has a thickness of about 0.0001-0.1 µm. In one embodiment, the polymer coating as applied to the solid substrates of this invention has a thickness of about 20-200 µm. In one embodiment, the polymer coating as applied to the solid substrates of this invention has a thickness of about 100-1500 µm.

In some embodiments, the polymer as applied to the bone growth promoting materials of this invention is a thin coating, which is associated with the bone growth promoting materials of this invention and has a thickness as indicated hereinabove.

In some embodiments, the polymer as applied to the bone growth promoting materials of this invention is applied throughout the bone growth promoting materials of this invention, such that, in some embodiments, the pores and voids within the bone growth promoting materials of the invention may be filled with polymers as herein described, and such polymer layer as applied may have a thickness of about 60-900 µm.

In some embodiments, multiple bone growth promoting materials comprising polymeric additives are implanted into a desired implantation site, wherein the polymer thickness applied to a first bone growth promoting material may vary as compared to a polymer thickness as applied to a second bone graft promoting coral-based material, implanted in the desired site. Variations in such thickness may reflect the range described herein.

In one embodiment, the thickness of the polymer as applied to the bone growth promoting materials of this invention influences physical characteristics of a bone growth promoting material of this invention. For example, the thickness of a polymeric application may influence elasticity, tensile strength, adhesiveness, or retentiveness, or any combination thereof of bone growth promoting material of this invention. In one embodiment, the polymer application increases the elasticity of a bone growth promoting material of this invention. In one embodiment, a polymeric application increases the tensile strength of a bone growth promoting material of this invention. In one embodiment, the adhesiveness of a polymeric application relates to adhesion of mesencymal stem cells, blood vessels, tissue at a site of desired repair. In one embodiment, a polymeric application decreases the adhesiveness of a bone growth promoting material of this invention. In one embodiment, a polymeric application increases the adhesiveness of a bone growth promoting material of this invention. One skilled in the art will recognize that a polymeric application may increase adhesiveness for an item while decreasing adhesiveness for another item. For example, in one embodiment, the polymeric application increases adhesiveness for a mesenchymal stem cell and decreases adhesiveness of an infective agent. In one embodiment, the retentiveness of a polymeric application relates to retention of a cell population. In one embodiment, the cell population retained within a polymer coating is a mesenchymal stem cell population, chondrocyte population osteoblast population, etc. In one embodiment, the retentiveness of a polymeric application relates to retention of effector compounds.

In one embodiment, the thickness of the polymeric application influences proliferation and/or differentiation of cells applied to or in contact with the bone growth promoting material of this invention, or influences the activation or migration of cells associated with cell or tissue growth/restored function to the devices of this invention, or a combination thereof.

In one embodiment, the bone growth promoting materials of this invention may further comprise an effector compound, which in some embodiments, may be associated directly with the bone graft promoting coral-based material of this invention, or in some embodiments, may be associated with a polymer, and applied in connection therewith.

In one embodiment, such effector compounds might include silver ions, copper ions or other metals, or combinations thereof. In another embodiment release of this compound might be facilitated by the application of electrical charge.

In one embodiment of this invention, the effector compound comprises a cytokine, a bone morphogenetic protein (BMP), growth factors, a chelator, a cell population, a therapeutic compound, or an antibiotic, or any combination thereof.

In one embodiment of this invention, the phrase "a therapeutic compound" refers to a peptide, a protein or a nucleic acid, or a combination thereof. In another embodiment, the therapeutic compound is an antibacterial, antiviral, antifungal or antiparasitic compound. In another embodiment, the therapeutic compound has cytotoxic or anti-cancer activity. In another embodiment, the therapeutic compound is an enzyme, a receptor, a channel protein, a hormone, a cytokine or a growth factor. In another embodiment, the therapeutic compound is immunostimulatory. In another embodiment, the therapeutic compound inhibits inflammatory or immune responses. In one embodiment, the therapeutic compound comprises a pro-angiogenic factor.

In one embodiment, the effector compound comprises, an anti-helminth, an antihistamine, an immunomodulatory, an anticoagulant, a surfactant, an antibody, a beta-adrenergic receptor inhibitor, a calcium channel blocker, an ace inhibitor, a growth factor, a hormone, a DNA, an siRNA, or a vector or any combination thereof.

In one embodiment, the phrase "effector compound" refers to any agent or compound, which has a specific purpose or application which is useful in the treatment, prevention, inhibition, suppression, delay or reduction of incidence of infection, a disease, a disorder, or a condition, when applied to the solid substrates, kits and/or methods of this invention. An effector compound of this invention, in one embodiment, will produce a desired effect which is exclusive to the ability to image the compound. In some embodiments, the effector compound may be useful in imaging a site at which the compound is present, however, such ability is secondary to the purpose or choice of use of the compound.

In one embodiment of this invention, term "effector compound" is to be understood to include the terms "drug" and "agent", as well, when referred to herein, and represents a molecule whose incorporation within the devices and/or methods of this invention, or whose use thereof, is desired. In one embodiment, the agent is incorporated directly within a bone graft promoting coral-based material of this invention. In another embodiment, the agent is incorporated within a bone graft promoting coral-based material of this invention, either by physical interaction with a polymer coating, a coral, or coral particles of this invention, or association thereto.

In one embodiment, the "effector compound" is a therapeutic compound.

In one embodiment, the phrase "a therapeutic compound", refers to a molecule, which when provided to a subject in need, provides a beneficial effect. In some cases, the molecule is therapeutic in that it functions to replace an absence or diminished presence of such a molecule in a subject. In one embodiment, the molecule is a nucleic acid coding for the expression of a protein is absent, such as in cases of an endogenous null mutant being compensated for by expression of the foreign protein. In other embodiments, the endogenous protein is mutated, and produces a non-functional protein, compensated for by the expression of a heterologous functional protein. In other embodiments, expression of a heterologous protein is additive to low endogenous levels, resulting in cumulative enhanced expression of a given protein. In other embodiments, the molecule stimulates a signaling cascade that provides for expression, or secretion, or others of a critical element for cellular or host functioning.

In another embodiment, the therapeutic compound may be natural or non-natural insulins, amylases, proteases, lipases, kinases, phosphatases, glycosyl transferases, trypsinogen, chymotrypsinogen, carboxypeptidases, hormones, ribonucleases, deoxyribonucleases, triacylglycerol lipase, phospholipase A2, elastases, amylases, blood clotting factors, UDP glucuronyl transferases, ornithine transcarbamoylases, cytochrome p450 enzymes, adenosine deaminases, serum thymic factors, thymic humoral factors, thymopoietins, growth hormones, somatomedins, costimulatory factors, antibodies, colony stimulating factors, erythropoietin, epidermal growth factors, hepatic erythropoietic factors (hepatopoietin), liver-cell growth factors, interleukins, interferons, negative growth factors, fibroblast growth factors, transforming growth factors of the $\alpha$ family, transforming growth factors of the family, gastrins, secretins, cholecystokinins, somatostatins, serotonins, substance P, transcription factors or combinations thereof.

In any of the embodiments herein, solid substrates, and their use in the methods of the present invention may further comprise, or be implanted with, other compounds such as, for example, antioxidants, growth factors, cytokines, antibiotics, anti-inflammatories, immunosuppressors, preservative, pain medication, other therapeutics, and excipient agents. In one embodiment, examples of growth factors that may be administered in addition to the HMG-CoA reductase inhibitor include, but are not limited to, epidermal growth factor (EGF), transforming growth factor-alpha (TGF-$\alpha$), transforming growth factor-beta (TGF-$\beta$), human endothelial cell growth factor (ECGF), granulocyte macrophage colony stimulating factor (GM-CSF), bone morphogenetic protein (BMP), nerve growth factor (NGF), vascular endothelial growth factor (VEGF), fibroblast growth factor (FGF), insulin-like growth factor (IGF), cartilage derived morphogenetic protein (CDMP), platelet derived growth factor (PDGF), or any combinations thereof. Examples of antibiotics include antimicrobials and antibacterials.

In any of the embodiments herein, solid substrates, and their use in the methods of the present invention may further comprise, or be implanted with, plasma, platelet rich plasma, any growth factor as appropriate, any glycosaminoglycan, in particular, hyaluronic acid and any useful form of same, or any combination of same.

In one embodiment, effector compounds for use in a solid substrate and/or a kit of this invention and/or a method of this invention may comprise, inter-alia, an antibody or antibody fragment, a peptide, an oligonucleotide, a ligand for a biological target, an immunoconjugate, a chemomimetic functional group, a glycolipid, a labelling agent, an enzyme, a metal ion chelate, an enzyme cofactor, a cytotoxic compound, a bactericidal compound, a bacteriostatic compound, a fungicidal compound, a fungistatic compound, a chemotherapeutic, a growth factor, a hormone, a cytokine, a toxin, a prodrug, an antimetabolite, a microtubule inhibitor, a radioactive material, or a targeting moiety, or any combination thereof.

In one embodiment, the bone graft promoting coral-based material and/or methods of this invention comprise or make use of an oligonucleotide, a nucleic acid, or a vector. In some embodiments, the term "oligonucleotide" is interchangeable with the term "nucleic acid", and may refer to a molecule, which may include, but is not limited to, prokaryotic sequences, eukaryotic mRNA, cDNA from eukaryotic mRNA, genomic DNA sequences from eukaryotic (e.g., mammalian) DNA, and even synthetic DNA sequences. The term also refers to sequences that include any of the known base analogs of DNA and RNA.

The bone growth promoting material and/or methods of use of this invention may comprise nucleic acids, in one embodiment, or in another embodiment, the solid substrates and/or kits of this invention and/or methods of use of this invention may include delivery of the same, as a part of a particular vector. In one embodiment, polynucleotide segments encoding sequences of interest can be ligated into commercially available expression vector systems suitable for transducing/transforming mammalian cells and for directing the expression of recombinant products within the transduced cells. It will be appreciated that such commercially available vector systems can easily be modified via commonly used recombinant techniques in order to replace, duplicate or mutate existing promoter or enhancer sequences and/or introduce any additional polynucleotide sequences such as for example, sequences encoding additional selection markers or sequences encoding reporter polypeptides.

In one embodiment, effector compounds for use in a solid substrate and/or a kit of this invention and/or a method of this invention may comprise, inter-alia, a cytokine, a bone morphogenetic protein (BMP), growth factor, a chelator, a cell population, a therapeutic compound, an anti-inflammatory compound, a pro-angiogenic compound or an antibiotic, or any combination thereof.

In one embodiment of this invention, the cells or tissue as used in accordance with the devices and/or methods of this invention, are engineered to express a desired product.

In one embodiment, the phrase "a cell population" refers to a transfected cell population, a transduced cell population, a transformed cell population, or a cell population isolated from a subject, or a combination thereof. In some embodiments, transfected, transduced or transformed cells, may be seeded on the bone graft promoting coral-based material, or in some embodiments, may be incorporated into a polymeric application thereto, or a combination thereof.

In one embodiment, a cell population of this invention comprises mesenchymal stem cells. In one embodiment, the mesenchymal stem cells are transformed.

In one embodiment, a cell population comprises cells beneficial in repair of a tissue for which the implantation of a bone growth promoting material of this invention is desired.

In some embodiments, the cells are beneficial in and/or promote bone formation and/or repair. Such cells may include chondroblasts or chondrocytes; fibrochondrocyte; osteocyte; osteoblast; osteoclast; synoviocyte; bone marrow cell; stromal cell; stem cell; embryonic stem cell; precursor cell, derived from adipose tissue; peripheral blood progenitor cell; stem cell isolated from adult tissue; genetically transformed cell; or a combination thereof. In another embodiment, a precursor cell may refer to a combination of chondrocytes and other cells; a combination of osteocytes and other cells; a combination of synoviocytes and other cells; a combination of bone marrow cells and other cells; a combination of mesenchymal cells and other cells; a combination of stromal cells and other cells; a combination of stem cells and other cells; a combination of embryonic stem cells and other cells; a combination of precursor cells isolated from adult tissue and other cells; a combination of peripheral blood progenitor cells and other cells; a combination of stem cells isolated from adult tissue and other cells; and a combination of genetically transformed cells and other cells. The precursor cells for use in the method of the present invention are prepared from an organ tissue of the recipient mammal (i.e. autologous), or a syngeneic mammal. In another embodiment, allogeneic and xenogeneic precursor cells may be utilized.

In one embodiment, the bone growth promoting material of this invention incorporates stem or progenitor or precursor cells. Such cells can be obtained directly from a mammalian donor, e.g., a patient's own cells, from a culture of cells from a donor, or from established cell culture lines. In some embodiments, the mammal is a mouse, rat, rabbit, guinea pig, hamster, cow, pig, horse, goat, sheep, dog, cat, monkey, ape or a human. Cells of the same species and/or of the same immunological profile can be obtained by biopsy, either from the patient or a close relative. Using standard cell culture techniques and conditions, the cells are then grown in culture until confluent and used when needed. The cells may be cultured until a sufficient number of cells have been obtained for a particular application.

In one embodiment, the bone growth promoting material of this invention incorporates any cell which may participate in tissue repair, for example, in bone fusion, formation or repair. In some embodiments, such cells represent autografts, in that cells are cultured ex-vivo to seed the cells on the bone graft promoting coral-based materials of the invention, and such seeded bone growth promoting materials are implanted into the subject.

In particular, this invention provides the unexpected application that the bone fusion devices of this invention provide improved prosthetic implants used to facilitate fusion between two or more bones or two or more portions of a bone, which is surprisingly improved when the bone growth promoting material is characterized by a specific fluid uptake capacity value of at least 75%, which specific fluid uptake capacity value was determined by establishing a spontaneous fluid uptake value divided by a total fluid uptake value or when the bone growth promoting material is characterized by having a contact angle value of less than 60 degrees, when in contact with a fluid.

In some aspects, the invention provides for the unique and surprising finding that the bone fusion devices of this invention comprise an outer cage frame maximizing exposure of the bone growth promoting material contained therein for contact with the bone surfaces coming into contact with the device. In some embodiments, the bone growth promoting material has been machined to include a modified surface of the bone growth promoting material such as the inclusion of ridges or reduced planes which allow for perfect fit with the outer cage frame elements containing the bone growth promoting material, such that the connection between the two is seamless. Such seamless juncture relates to the potential for an outer facing surface of the bone growth promoting material to only minimally jut out or below from an outer surface of the outer cage frame elements, or not at all, so that effectively a seamless surface is provided. Surprisingly, the maximizing of the exposure of the bone growth promoting materials to the treated bone provides for a surprising and unexpected qualitative and, in some embodiments, quantitative improvement in the bone repair/fusion.

In some embodiments, multiple bone growth promoting materials as herein described are incorporated within the devices and/or for use in the methods of this invention to effect greater bone repair.

In one embodiment, the phrase "bone repair" refers to restoring a bone defect to a more healthful state and in some embodiments, specifically contemplates optimal intra-vertebral fusion. In one embodiment, same promotes regeneration of bone tissue. In one embodiment, same promotes the filling in of any fracture or void within the affected vertebrae. In one embodiment, same promotes complete or partial regeneration of bone tissue at a site of bone repair.

The devices and/or methods of the invention may also find application in treating/improving/reducing symptoms and/or pain associated with conditions caused by factors including and in some embodiments, factors other than bone remodeling disorders. Such bone deficits include fractures, bone trauma, and others.

In some embodiments, the bone growth promoting material is processed to optimize incorporation and optimal repair. In some embodiments, such processing may comprise cutting, sanding or otherwise smoothing the surface of the bone graft promoting coral-based material, for optimal repair.

It will be apparent to those skilled in the art that various modifications and variations can be made in the bone growth promoting materials, without departing from the spirit or scope of the invention.

In some embodiments, the method further comprises customizing a bone growth promoting material as herein described, or at least one of the surfaces of same for optimal effect.

In some embodiments, such customization includes predicting and designing a best fit and idealized, customized procedure and bone growth promoting material for implantation in a subject, promoting greater and more complete healing in the subject.

In some embodiments, the methods of this invention lend themselves to use of an automated system, suitable for use with any combination of bone growth promoting material as herein described.

In some aspects, such automated systems are suitable for robotic assemblies to produce desired movements of the machinery preparing and implanting the fusion devices of this invention and/or components of same and/or implantation of same.

In some aspects, such automated systems are well established and allow for greater precision and control during surgical implantation procedures and may be further combined with the customized devices and/or methods as herein described to provide idealized implantations and optimal results in a subject in need of same.

In some embodiments, the term "comprise" or grammatical forms thereof, refers to the inclusion of the indicated components of this invention, as well as inclusion of other active agents, and pharmaceutically acceptable carriers, excipients, emollients, stabilizers, etc., as are known in the pharmaceutical industry.

In one embodiment, the term "about" refers to a variance of from 1-10%, or in another embodiment, 5-15%, or in another embodiment, up to 10%, or in another embodiment, up to 25% variance from the indicated values, except where context indicates that the variance should not result in a value exceeding 100%.

In one embodiment, the present invention provides combined preparations. In one embodiment, the term "a combined preparation" defines especially a "kit of parts" in the sense that the combination partners as defined above can be used independently or in different combinations i.e., simultaneously, concurrently, separately or sequentially.

EXAMPLES

Example 1

Preparing Optimized Intervertebral Fusion Devices of this Invention

Materials and Methods

For preparation of the bone graft promoting coral-based material a diamond saw is used to remove an outer coral layer, and large sections from which representative smaller sections of desired dimensions are cut from the coral block.

Coral from the hydrocoral *Porites lutea* which has an average pore size of 100-150 μm is harvested from various regions within a coral. The coral is evaluated visually for its appearance, density, and porosity. Coral wis then optionally immersed in 5% sodium hypochlorite for removal of external organic tissue. Briefly, coral is first exposed to a 5% sodium hypochlorite solution for 30 minutes, 3 exchanges at temperature range of from RT-50° C., and sub-atmospheric pressure using vacuum pressure ranging from 0.2-0.00001 Bar. The coral sections are then exposed to a 10% solution of hydrogen peroxide for 15 minutes at a temperature range of from RT-50° C., and sub-atmospheric pressure using vacuum pressure ranging from 0.2-0.00001 Bar. The cleaned sections are then washed in distilled water for 30 minutes, 3 exchanges at a temperature range of from RT-50° C., and sub-atmospheric pressure using vacuum pressure ranging from 0.3-0.00001 Bar.

The coral is optionally sterilized by exposure to gamma radiation at a strength of at least 22.5 kGy and can then be stored aseptically, in packaging material, and in particular, the smaller samples are irradiated, whereas larger blocks assessed may not be irradiated.

Each section is then place in a plastic petri dish and 2 ml of fluid is applied to each dish. Observations regarding absorption of the fluid are recorded. Fluids used include animal blood, plasma, water and various colored solutions.

Coral samples with substantial absorption throughout the structure are used.

Additional coral samples were taken from identical regions as to those thus identified above as absorptive, and the samples are isolated and machined to a desired size and shape, then dried.

A dry weight for each sample is recorded.

Water is added to each assay container in an approximately 1:1 ratio or slightly more, i.e. equal to or slightly more than the size of the sample in mm as compared to the volume of fluid in ml is added to the container.

The sample is then weighed and a spontaneous fluid uptake value determined.

A significantly increased amount of fluid is then brought into contact with the sample and a vacuum applied for a period of time to ensure maximal uptake of the applied fluid into the coral sample, and total fluid uptake capacity is assessed and the specific fluid uptake capacity value determined by dividing the spontaneous fluid uptake value by the total fluid uptake capacity. Samples with a value of 75% or more were selected.

Samples are then further machined to allow for recesses being created which provide an essentially perfect and seamless fit with a cage frame element, maximizing surface exposure of the coral for contact with treated bone, while providing a sufficiently sturdy and stabilizing cage frame that can be affixed to the treated region.

Example 2

Embodied Bone Fusion Devices of this Invention

FIG. 1A-1C schematically describes a bone fusion device (1-100) of this invention. The device comprises cage frame and a bone graft promoting coral-based material. Referring to FIG. 1C, the cage frame 1-40 is seen, which comprises a bracketing structure 1-50, which serves to frame bone graft promoting coral-based material which is machined to include complementary crevices, such that the bracketing structure is surrounded by the bone graft promoting coral-based material, which protrudes apically, basally and laterally such that the cage frame bracketing structure is effectively seamlessly nestled within and around the bone graft promoting coral-based material.

Thus, the cage frame bracketing structure contains windowed regions 1-60 which are then filled by protruding machined surfaces 1-20 of the bone graft promoting coral-based material.

The cage frame will also comprise an affixing region 1-70, containing access regions 1-80 through which affixing structures may be inserted to anchor the device to the bone being thereby treated.

FIGS. 2A-2F depict embodied bone fusion device of this invention. The device comprises a cage frame 2-50 and a bone graft promoting coral-based material 2-10. Referring to FIGS. 2A and 2D, the bone graft promoting coral-based material 2-10 is contoured on a surface to provide a curved profile. The bone graft promoting coral-based material is also machined to provide surface exposed regions 2-20, and recessed regions 2-30, flanked by recessing regions 2-25, into which bracketing structures of the cage frame 2-55 insert in a tight fit manner such that the outer exposed surface of the bone graft promoting coral-based material and the outer surface of the cage frame are seamed together in an essentially perfect fit such that the junction regions between the two (See FIGS. 2B and 2C in this regard).

FIGS. 2E and 2G depict a different surface of the bone fusion device depicted in FIGS. 2A-2B, where the exposed surface depicted is not contoured, indicating that one or more surfaces of the bone fusion devices of this invention may be contoured or not to provide a curved or other geometrically adapted surface, other than a flat surface.

Example 3

Figures 3A, 3B:
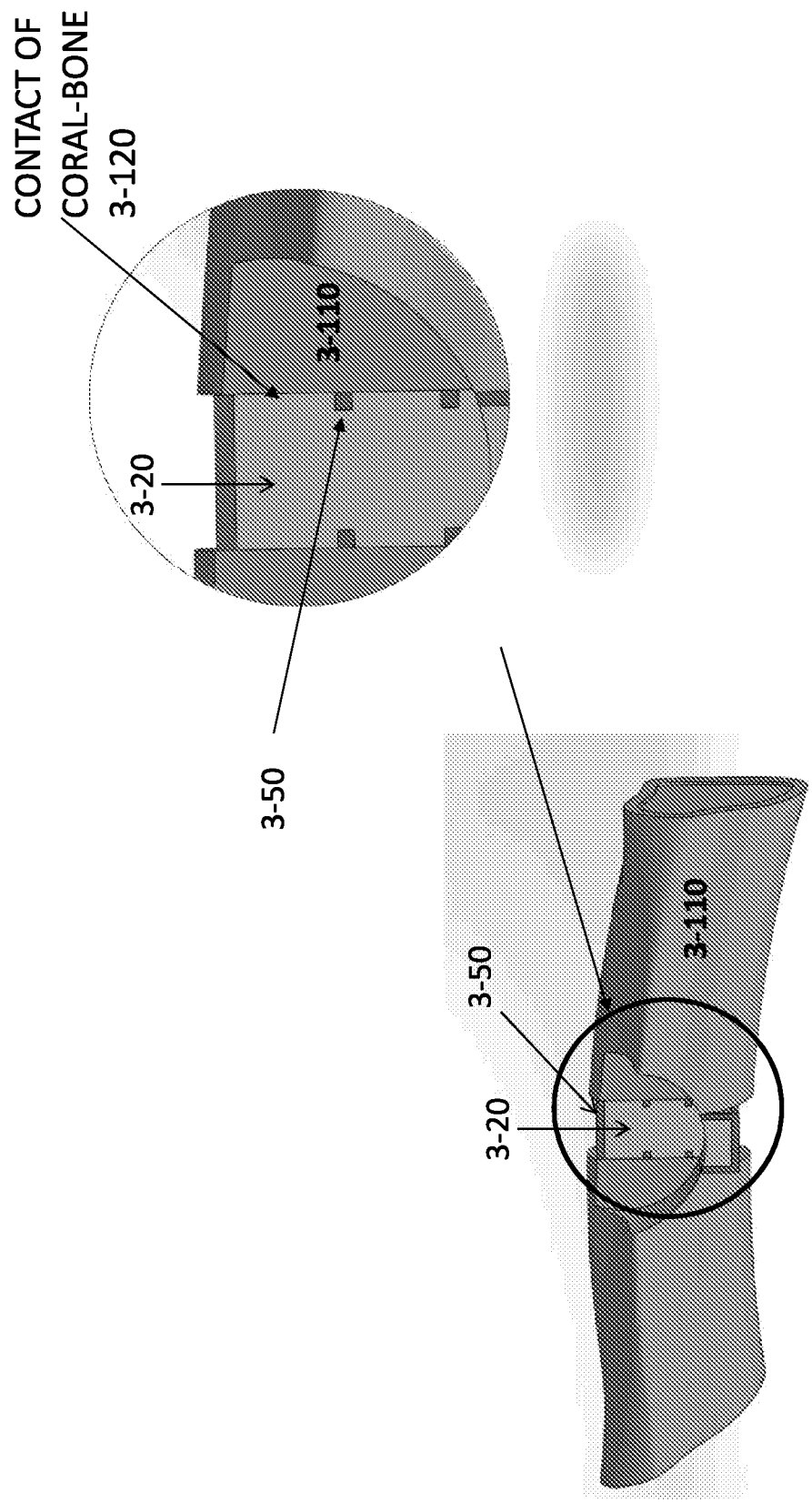
FIGS. 3A and 3B depict another embodied bone fusion device, highlighting exposed surfaces of the bone growth promoting material, available for contact with native bone to which the device is being applied.

Improved Bone Fusion Unique to Incorporation of the Bone Fusion Devices of this Invention Bone fusion devices are prepared as described in Example 1 and the overall shape and size will be in consideration of the application to which same is being applied. For example, and referring to FIGS. 3A and 3B depict an embodied means of joining two bone structures 3-110 or portions of a bone structure, where the growth promoting material 3-20 is shown contained within the cage frame 3-50, providing a framework for the coral, to promote union between the left and right sides, where the interface or contact region 3-120 between the bone growth promoting material, such as coral, and adjacent bone is depicted.

Example 4

In Vivo Improved Bone Fusion Unique to Incorporation of the Bone Fusion Devices of this Invention Bone fusion devices were constructed and prepared as depicted in FIG. 2C-2D and FIG. 4A. The devices were implanted in 6 goats subjected to a Tibial Tuberosity Advancement surgery (TTA). The cage component was constructed of titanium and the bone growth promoting material was comprised of coral prepared as described in Example 1.

FIGS. 4B-4E are photographs of the surgical implantation procedure securing the implants in each animal Goats initially are unable to walk freely, exhibiting a limp and otherwise altered gate, as is known in the art, in use of this model.

By 2 months following the surgery all treated animals were found to walk freely, with no signs of limping and an endpoint of 6 months post implantation was established, when animals are sacrificed and a micro CT and histologic evaluation are performed, where excellent osteointegration with bone remodeling is observed.

Figure 5A:
FIG. 5A-5E depicts another embodied bone fusion device depicted schematically in FIG. 6A-6B, and implantation of same in a non-union fracture in the leg of a dog. The white arrows in FIGS. 5A and 5B show the fracture resulting in discontinuous bone and the white arrows in FIGS. 5C and 5D show filled in bone at these locations, as determined by CT, following implantation. The striped arrow indicates newly formed bone in the defect site, remodeled from the coral, and the black arrow indicates the frame location.
Figure 5B:
Figure 5C:
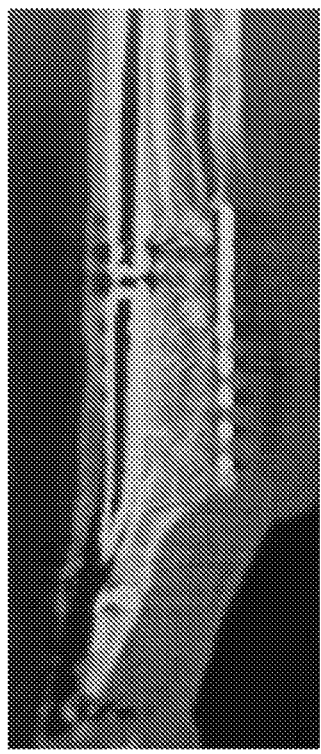
Figure 5D:
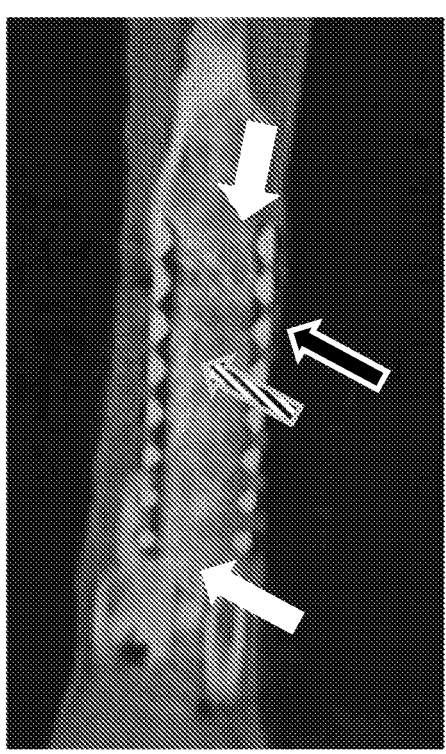
Figure 5E:
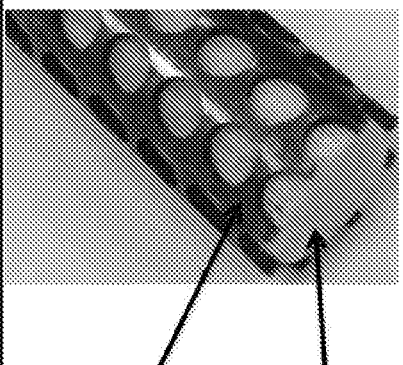

FIGS. 5A-5E and FIG. 6 depict the results of in vivo studies conducted in dogs in which an embodied bone fusion device of this invention is implanted in a non-union fracture within the leg of the dog. FIGS. 5A-5B are X-ray films showing the non-union fracture in the animal (white arrows). An embodied bone fusion device of this invention, as depicted in FIG. 5E was surgically implanted and secured so that the long axis of the implant was inserted in the region of the non-union fracture, aligning the long axis of the implant with the area between the two non-adjoining bones to bridge same. As is evident from FIG. 5E, the coral bone growth promoting material 5-20 at the terminus of the device maximized contact between adjacent bone to which the device is applied, so that the fractured bone is in direct, maximized contact with the coral. The cage 5-50 provides structural support and the other terminus of the device similarly maximizes contact between the second non-adjoining bone and coral bone growth promoting material maximally exposed at the second terminus, as well.

FIGS. 5C and 5D depict CT images taken 12 months post-implantation, which demonstrate the superior remodeling of the coral scaffold into newly formed bone bridging the gap (see white arrows) resulting in full healing of the fracture. The dog is fully mobile and pain and symptom free following the procedure.

Figure 6:
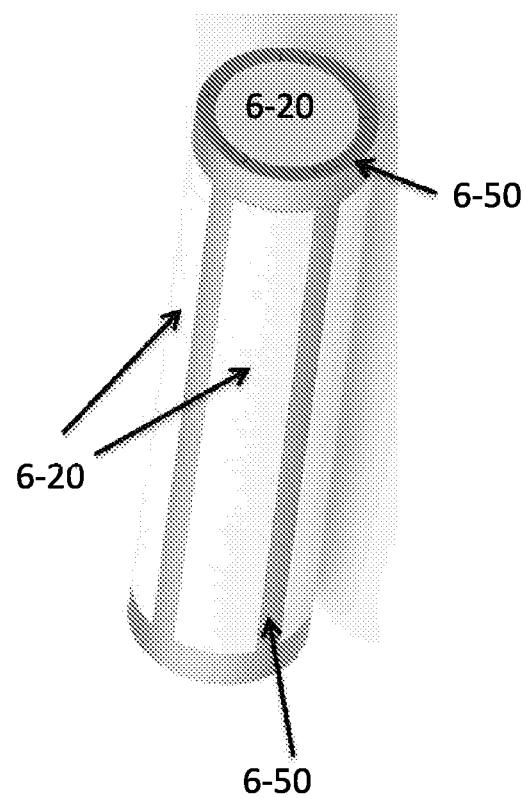
FIG. 6 depicts another embodied bone fusion device, in which the bone growth promoting material (6-20) extends to be flush with the terminus of the titanium cage (6-50) and to maximize surface exposure of the bone growth promoting material (6-20).

FIG. 6 depicts a further example of a similar embodied bone fusion device as used in the in vivo study described in FIG. 5E, where the cage 6-50 component provides support for the coral bone growth promoting material 6-20, which is maximized in placement to interact with bone, so that the termini of the device comprise substantially exposed bone growth promoting material, while being supported by a cage 6-50 giving maximal support for this geometry.

It will be understood by those skilled in the art that various changes in form and details may be made therein without departing from the spirit and scope of the invention as set forth in the appended claims. Those skilled in the art will recognize, or be able to ascertain using no more than routine experimentation, many equivalents to the specific embodiments of the invention described herein. Such equivalents are intended to be encompassed in the scope of the claims.

In one embodiment of this invention, "about" refers to a quality wherein the means to satisfy a specific need is met, e.g., the size may be largely but not wholly that which is specified but it meets the specific need of cartilage repair at a site of cartilage repair. In one embodiment, "about" refers to being closely or approximate to, but not exactly. A small margin of error is present. This margin of error would not exceed plus or minus the same integer value. For instance, about 0.1 micrometers would mean no lower than 0 but no higher than 0.2. In some embodiments, the term "about" with regard to a reference value encompasses a deviation from the amount by no more than 5%, no more than 10% or no more than 20% either above or below the indicated value.

In the claims articles such as "a", "an" and "the" mean one or more than one unless indicated to the contrary or otherwise evident from the context. Claims or descriptions that include "or" or "and/or" between members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention provides, in various embodiments, all variations, combinations, and permutations in which one or more limitations, elements, clauses, descriptive terms, etc., from one or more of the listed claims is introduced into another claim dependent on the same base claim unless otherwise indicated or unless it would be evident to one of ordinary skill in the art that a contradiction or inconsistency would arise. Where elements are presented as lists, e.g. in Markush group format or the like, it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in haec verba herein. Certain claims are presented in dependent form for the sake of convenience, but Applicant reserves the right to rewrite any dependent claim in independent format to include the elements or limitations of the independent claim and any other claim(s) on which such claim depends, and such rewritten claim is to be considered equivalent in all respects to the dependent claim in whatever form it is in (either amended or unamended) prior to being rewritten in independent format.

What is claimed is:

1. An intervertebral fusion device adapted to form a rigid structure between a first vertebra and a second vertebra, the intervertebral fusion device comprising:
    a cage frame defined by a plurality of cage frame elements including a top cage frame element sized and configured to engage the first vertebra, a bottom cage frame element sized and configured to engage the second vertebra, an anterior cage frame element, a posterior cage frame element, and one or more lateral cage frame elements, the top cage frame element adapted to be load bearing for the first vertebra, the bottom cage frame element adapted to be load bearing for the second vertebra; the posterior cage frame element including an opening to receive a bone growth promoting material;
    each of the plurality of cage frame elements having a peripheral edge contoured to not be sharp along its entire length;
    at least one of the top and bottom cage frame elements includes a plurality of ridges to engage a surface of an adjacent vertebrae, and the ridges are spaced from peripheral edges of the cage frame element;
    a bone growth promoting material disposed within the cage frame through said opening of the posterior cage frame element, the bone growth promoting material comprising:
        a solid block having a shape complementary to an internal chamber of the cage frame, the solid block having an outer surface; and
        a plurality of grooves formed within the outer surface, at least some of the plurality of grooves complementary to and adapted to accommodate at least some of the plurality of cage frame elements therein such that the outer surface of the bone growth promoting material is neither protruding nor recessed with respect to at least some of the plurality of cage frame elements;
    wherein the bone growth promoting material comprises one or more solid coral pieces, or ground coralline-based material pieces or a combination thereof,
    wherein the bone growth promoting material is characterized by a specific fluid uptake capacity value of at least 75%.

2. The intervertebral fusion device of claim 1, wherein the cage includes a memory metal.

3. The intervertebral fusion device of claim 1, wherein the cage is adapted to form a modular component.

4. The intervertebral fusion device of claim 1, wherein the cage is adapted to be stackable with at least another cage.

5. The intervertebral fusion device of claim 1, wherein the cage comprises stainless steel, titanium, chrome, cobalt, polycarbonate, polypropylene, polyethylene, polymethylmethacrylate, polysulfone filled with glass or carbon fibers, nitinol, PEEK, a ceramic material, hydroxyapatite coated hard materials or a combination thereof.

6. The intervertebral fusion device of claim 1, wherein the coralline-based material is an enriched coralline-based material that is enriched for silicium.

7. The intervertebral fusion device of claim 1, wherein the cage frame, the bone growth promoting material or a combination thereof may be prepared according to any geometry suitable to accommodate within a desired site of bone repair or bone joining.

8. The intervertebral fusion device of claim 7, wherein the geometry is customized based on medical imaging assessments of the site of bone repair or bone joining.

9. The intervertebral fusion device of claim 8, wherein the medical imaging assessment comprises CT or MRI scanning.

10. The intervertebral fusion device of claim 1, wherein the bone growth promoting material is isolated from a *Porites* species, a *Goniopora*, a *Millepora* species or an *Acropora* species.

11. A method for stabilizing a first vertebra and a second vertebra relative to one another, the method comprising:
    disposing the intervertebral fusion device of claim 1 between the first and second vertebrae; and
    securing the intervertebral fusion device between the first and second vertebrae to inhibit movement of the first and second vertebrae relative to one another, even when the first and second vertebrae are subject to forces other than perpendicular compressive forces.

* * * * *